US011155872B2

(12) United States Patent
Schutz et al.

(10) Patent No.: US 11,155,872 B2
(45) Date of Patent: Oct. 26, 2021

(54) DETECTION AND QUANTIFICATION OF DONOR CELL-FREE DNA IN THE CIRCULATION OF ORGAN TRANSPLANT RECIPIENTS

(71) Applicant: CHRONIX BIOMEDICAL, San Jose, CA (US)

(72) Inventors: Ekkehard Schutz, Gottingen (DE); Julia Beck, Gottingen (DE)

(73) Assignee: Chronix Biomedical, San Jose, CA (US)

(*) Notice: Subject to any disclaimer, the term of this patent is extended or adjusted under 35 U.S.C. 154(b) by 136 days.

(21) Appl. No.: 15/920,356

(22) Filed: Mar. 13, 2018

(65) Prior Publication Data

US 2018/0346982 A1    Dec. 6, 2018

Related U.S. Application Data

(63) Continuation of application No. 14/893,807, filed as application No. PCT/US2014/040055 on May 29, 2014, now abandoned.

(60) Provisional application No. 61/828,553, filed on May 29, 2013.

(51) Int. Cl.
| | |
|---|---|
| C12Q 1/68 | (2018.01) |
| C12P 19/34 | (2006.01) |
| C12Q 1/6883 | (2018.01) |
| G01N 33/68 | (2006.01) |
| C12Q 1/6881 | (2018.01) |

(52) U.S. Cl.
CPC ......... *C12Q 1/6883* (2013.01); *C12Q 1/6881* (2013.01); *G01N 33/6854* (2013.01); *C12Q 2600/106* (2013.01); *C12Q 2600/156* (2013.01); *C12Q 2600/16* (2013.01); *C12Q 2600/172* (2013.01); *G01N 2800/245* (2013.01)

(58) Field of Classification Search
CPC ............ C12Q 1/6883; C12Q 2600/106; C12Q 2600/156; G01N 2800/245
See application file for complete search history.

(56) References Cited

U.S. PATENT DOCUMENTS

| 2010/0209926 A1 | 8/2010 | Alaoui et al. |
| 2012/0115737 A1 | 5/2012 | Ehrich et al. |

FOREIGN PATENT DOCUMENTS

| EP | 1325963 A1 | 9/2003 |
| WO | 2008/098142 A2 | 8/2008 |
| WO | 2012/115851 A1 | 8/2012 |
| WO | 2013/159035 A2 | 10/2013 |
| WO | 2015/138997 A1 | 9/2015 |

OTHER PUBLICATIONS

Submitted SNP(ss) Report in Submission Format, Human1M-Duov3_B_GA002729-0_T_F_1533418701, NCBI Assay Id(ss#): ss 168890814, Reference SNP Id(rs#): rs741384 (Oct. 1, 2009) (Year: 2009).*
U.S. Appl. No. 14/893,807, "Non-Final Office Action," dated Sep. 14, 2017, 25 pages.
International Search Report and Written Opinion dated Nov. 24, 2015 of International Patent Application No. PCT/US2014/040055, 14 pages.
Baruch E. et al. Animal Genetics, 39, 474-479 (2008).
Beck, et al., "Digital Droplet PCR for Rapid Quantification of Donor DNA in the Circulation of Transplant Recipients as a Potential Universla Biomarker of Graft Injury," Clinical Chemistry, vol. 59, No. 12, pp. 1732-1741 (2013).
Gineikiene E. et al. Journal of Molecular Diagnositics, vol. 11, No. 1, Jan. 2009.
Lima B. et al. Circulation, Jul. 4, 2006, vol. 114, Issue 1 suppl.
Snyder, et al., "Universal noninvasive detection of solid organ transplant rejection," Proceedings of the National Academy of Sciences, vol. 108, No. 15 pp., pp. 6229-6234 (2011).
Submitted SNP(ss) Details: ss238126804 (Jun. 20, 2011) from www.ncbi.nlm.nih.gov., 1 printed page.
Ying, et al., "Ready Detection of Donor-Specific Single-Nucleotide Polymorphisms in the Urine of Renal Transplant Recipients by Matrix-Assisted Laser Desorption/Ionization Time-of-Flight Mass Spectrometry," Clinical Chemistry, vol. 51, No. 10, pp. 1903-1904 (2005).
EP14804474.6, "Notice of Opposition," dated Aug. 8, 2019, 6 pages.
EP14804474.6 "Opposition Statement," dated Jul. 31, 2019, 31 pages.
Li et al., "Ready Detection of Donor-Specific Single Nucleotide Polymorphisms in the Urine of Renal Transplant Recipients by Matrix-Assisted Laser Desorption/Ionization Time-of-Flight Mass Spectroscopy," Clinical Chemistry 51, No. 10, 2005, pp. 1903-1904.
Hidestrand, et al., "Highly Sensitive Transplant Rejection Surveillance Using Targeted Detection of Donor Specific Cell Free DNA," The Journal of Heart and Lung Transplantation, 31:4S, 2012, pp. S91-S92.
Sparks, et al., "Noninvasive prenatal detection and selective analysis of cell-free DNA obtained from maternal blood: evaluation for trisomy 21 and trisomy 18," American Journal of Obstetrics & Gynecology, 2012, 206:319, pp. 319.e1-319.e9.

* cited by examiner

*Primary Examiner* — Stephen T Kapushoc
(74) *Attorney, Agent, or Firm* — Kilpatrick Townsend & Stockton LLP

(57) ABSTRACT

This invention provides methods, compositions, and kits relating to detecting donor cell-free DNA in the circulation of a transplant recipient for the early identification of transplant rejection or for detection of damage to transplant cells.

22 Claims, 11 Drawing Sheets
Specification includes a Sequence Listing.

SEQUENCE LISTING

```
<160> NUMBER OF SEQ ID NOS: 164

<210> SEQ ID NO 1
<211> LENGTH: 21
<212> TYPE: DNA
<213> ORGANISM: Artificial Sequence
<220> FEATURE:
<223> OTHER INFORMATION: synthetic forward amplification primer for
      target region containing SNP S43

<400> SEQUENCE: 1
gtctctgggg gtctgttggc c                                              21
```

<210> SEQ ID NO 2
<211> LENGTH: 21
<212> TYPE: DNA
<213> ORGANISM: Artificial Sequence
<220> FEATURE:
<223> OTHER INFORMATION: synthetic reverse amplification primer for
      target region containing SNP S43

<400> SEQUENCE: 2
agaggaagga ctcccagggg g                                         21

<210> SEQ ID NO 3
<211> LENGTH: 24
<212> TYPE: DNA
<213> ORGANISM: Artificial Sequence
<220> FEATURE:
<223> OTHER INFORMATION: synthetic forward amplification primer for
      target region containing SNP S46

<400> SEQUENCE: 3
tccagcagag gaaatagtac ttgc                                      24

<210> SEQ ID NO 4
<211> LENGTH: 20
<212> TYPE: DNA
<213> ORGANISM: Artificial Sequence
<220> FEATURE:
<223> OTHER INFORMATION: synthetic reverse amplification primer for
      target region containing SNP S46

<400> SEQUENCE: 4
agccacctgg tctcctttca                                           20

<210> SEQ ID NO 5
<211> LENGTH: 25
<212> TYPE: DNA
<213> ORGANISM: Artificial Sequence
<220> FEATURE:
<223> OTHER INFORMATION: synthetic forward amplification primer for
      target region containing SNP S38

<400> SEQUENCE: 5
tcaatcctca caacttccct aaggg                                     25

<210> SEQ ID NO 6
<211> LENGTH: 21
<212> TYPE: DNA
<213> ORGANISM: Artificial Sequence
<220> FEATURE:
<223> OTHER INFORMATION: synthetic reverseamplification primer for
      target region containing SNP S38

<400> SEQUENCE: 6
agtgggaggg aggtacagtg a                                         21

<210> SEQ ID NO 7
<211> LENGTH: 18
<212> TYPE: DNA
<213> ORGANISM: Artificial Sequence
<220> FEATURE:
<223> OTHER INFORMATION: synthetic forward amplification primer for
      target region containing SNP S48

<400> SEQUENCE: 7
ggggtgtggg gtgaggga                                             18

<210> SEQ ID NO 8
<211> LENGTH: 18
<212> TYPE: DNA
<213> ORGANISM: Artificial Sequence
<220> FEATURE:
<223> OTHER INFORMATION: synthetic reverse amplification primer for
      target region containing SNP S48

<400> SEQUENCE: 8
gcgcggctgg ggtgttta                                                 18

<210> SEQ ID NO 9
<211> LENGTH: 24
<212> TYPE: DNA
<213> ORGANISM: Artificial Sequence
<220> FEATURE:
<223> OTHER INFORMATION: synthetic forward amplification primer for
      target region containing SNP S50

<400> SEQUENCE: 9
tcttgtcgag gctgccctga aagg                                          24

<210> SEQ ID NO 10
<211> LENGTH: 18
<212> TYPE: DNA
<213> ORGANISM: Artificial Sequence
<220> FEATURE:
<223> OTHER INFORMATION: synthetic reverse amplification primer for
      target region containing SNP S50

<400> SEQUENCE: 10
acagagccgg ccggtcgc                                                 18

<210> SEQ ID NO 11
<211> LENGTH: 25
<212> TYPE: DNA
<213> ORGANISM: Artificial Sequence
<220> FEATURE:
<223> OTHER INFORMATION: synthetic forward amplification primer for
      target region containing SNP S51

<400> SEQUENCE: 11
ctgacccaat tgtgtgtgca gagca                                         25

<210> SEQ ID NO 12
<211> LENGTH: 26
<212> TYPE: DNA
<213> ORGANISM: Artificial Sequence
<220> FEATURE:
<223> OTHER INFORMATION: synthetic reverse amplification primer for
      target region containing SNP S51

<400> SEQUENCE: 12
tcttgagcac cttaccagcc ttcaca                                        26

<210> SEQ ID NO 13
<211> LENGTH: 22
<212> TYPE: DNA
<213> ORGANISM: Artificial Sequence
<220> FEATURE:
<223> OTHER INFORMATION: synthetic forward amplification primer for
      target region containing SNP S53

<400> SEQUENCE: 13
tgtgggcagt ctcactggag ca                                            22

```
<210> SEQ ID NO 14
<211> LENGTH: 20
<212> TYPE: DNA
<213> ORGANISM: Artificial Sequence
<220> FEATURE:
<223> OTHER INFORMATION: synthetic reverse amplification primer for
      target region containing SNP S53

<400> SEQUENCE: 14 accccccagtg tggctctgct                                                  20

<210> SEQ ID NO 15
<211> LENGTH: 22
<212> TYPE: DNA
<213> ORGANISM: Artificial Sequence
<220> FEATURE:
<223> OTHER INFORMATION: synthetic forward amplification primer for
      target region containing SNP S54

<400> SEQUENCE: 15
acctgccccc tagaaaactg ct                                                22

<210> SEQ ID NO 16
<211> LENGTH: 29
<212> TYPE: DNA
<213> ORGANISM: Artificial Sequence
<220> FEATURE:
<223> OTHER INFORMATION: synthetic reverse amplification primer for
      target region containing SNP S54

<400> SEQUENCE: 16
gcagtactat actagaaaca catggcagc                                         29

<210> SEQ ID NO 17
<211> LENGTH: 22
<212> TYPE: DNA
<213> ORGANISM: Artificial Sequence
<220> FEATURE:
<223> OTHER INFORMATION: synthetic forward amplification primer for
      target region containing SNP S55

<400> SEQUENCE: 17
cgccccaaat tgcgcacaac ca                                                22

<210> SEQ ID NO 18
<211> LENGTH: 23
<212> TYPE: DNA
<213> ORGANISM: Artificial Sequence
<220> FEATURE:
<223> OTHER INFORMATION: synthetic reverse amplification primer for
      target region containing SNP S55

<400> SEQUENCE: 18
acttccctcc caaccccacc act                                               23

<210> SEQ ID NO 19
<211> LENGTH: 20
<212> TYPE: DNA
<213> ORGANISM: Artificial Sequence
<220> FEATURE:
<223> OTHER INFORMATION: synthetic forward amplification primer for
      target region containing SNP S57

<400> SEQUENCE: 19
cagcctctgg ttccaggcct                                                   20

<210> SEQ ID NO 20
```

```
<211> LENGTH: 23
<212> TYPE: DNA
<213> ORGANISM: Artificial Sequence
<220> FEATURE:
<223> OTHER INFORMATION: synthetic reverse amplification primer for
      target region containing SNP S57

<400> SEQUENCE: 20
ggagaatccc agaagcaggc tga                                           23

<210> SEQ ID NO 21
<211> LENGTH: 21
<212> TYPE: DNA
<213> ORGANISM: Artificial Sequence
<220> FEATURE:
<223> OTHER INFORMATION: synthetic forward amplification primer for
      target region containing SNP S58

<400> SEQUENCE: 21
gtgcagcccc tgttcatgcc t                                             21

<210> SEQ ID NO 22
<211> LENGTH: 19
<212> TYPE: DNA
<213> ORGANISM: Artificial Sequence
<220> FEATURE:
<223> OTHER INFORMATION: synthetic reverse amplification primer for
      target region containing SNP S58

<400> SEQUENCE: 22
catgccaggc cagggtgg                                                 19

<210> SEQ ID NO 23
<211> LENGTH: 25
<212> TYPE: DNA
<213> ORGANISM: Artificial Sequence
<220> FEATURE:
<223> OTHER INFORMATION: synthetic forward amplification primer for
      target region containing SNP S59

<400> SEQUENCE: 23
agaaagaaag aagcagggaa gggac                                         25

<210> SEQ ID NO 24
<211> LENGTH: 22
<212> TYPE: DNA
<213> ORGANISM: Artificial Sequence
<220> FEATURE:
<223> OTHER INFORMATION: synthetic reverse amplification primer for
      target region containing SNP S59

<400> SEQUENCE: 24
tggagctaaa atgagcctgc gt                                            22

<210> SEQ ID NO 25
<211> LENGTH: 20
<212> TYPE: DNA
<213> ORGANISM: Artificial Sequence
<220> FEATURE:
<223> OTHER INFORMATION: synthetic forward amplification primer for
      target region containing SNP S63

<400> SEQUENCE: 25
gctgttgctg cctcacaggt                                               20

<210> SEQ ID NO 26
<211> LENGTH: 21
```

<212> TYPE: DNA
<213> ORGANISM: Artificial Sequence
<220> FEATURE:
<223> OTHER INFORMATION: synthetic reverse amplification primer for
      target region containing SNP S63

<400> SEQUENCE: 26
agggcaaagg caaatgcacc a                                           21

<210> SEQ ID NO 27
<211> LENGTH: 20
<212> TYPE: DNA
<213> ORGANISM: Artificial Sequence
<220> FEATURE:
<223> OTHER INFORMATION: synthetic forward amplification primer for
      target region containing SNP S66

<400> SEQUENCE: 27
accctgaccc tcagttcctt                                             20

<210> SEQ ID NO 28
<211> LENGTH: 25
<212> TYPE: DNA
<213> ORGANISM: Artificial Sequence
<220> FEATURE:
<223> OTHER INFORMATION: synthetic reverse amplification primer for
      target region containing SNP S66

<400> SEQUENCE: 28
aagagccctt ataaggtgtg agaaa                                       25

<210> SEQ ID NO 29
<211> LENGTH: 20
<212> TYPE: DNA
<213> ORGANISM: Artificial Sequence
<220> FEATURE:
<223> OTHER INFORMATION: synthetic forward amplification primer for
      target region containing SNP S67

<400> SEQUENCE: 29
atgaagagta agcggggccg                                             20

<210> SEQ ID NO 30
<211> LENGTH: 20
<212> TYPE: DNA
<213> ORGANISM: Artificial Sequence
<220> FEATURE:
<223> OTHER INFORMATION: synthetic reverse amplification primer for
      target region containing SNP S67

<400> SEQUENCE: 30
cggacccatt tcacccacca                                             20

<210> SEQ ID NO 31
<211> LENGTH: 20
<212> TYPE: DNA
<213> ORGANISM: Artificial Sequence
<220> FEATURE:
<223> OTHER INFORMATION: synthetic forward amplification primer for
      target region containing SNP S68

<400> SEQUENCE: 31
ggacactcac tggggcctct                                             20

<210> SEQ ID NO 32
<211> LENGTH: 27
<212> TYPE: DNA

```
<213> ORGANISM: Artificial Sequence
<220> FEATURE:
<223> OTHER INFORMATION: synthetic reverse amplification primer for
      target region containing SNP S68

<400> SEQUENCE: 32
aggactgaaa ctagaagaaa aggtcgg                                            27

<210> SEQ ID NO 33
<211> LENGTH: 22
<212> TYPE: DNA
<213> ORGANISM: Artificial Sequence
<220> FEATURE:
<223> OTHER INFORMATION: synthetic forward amplification primer for
      target region containing SNP S70

<400> SEQUENCE: 33
tggcccagtt agaaggtgtg ga                                                 22

<210> SEQ ID NO 34
<211> LENGTH: 20
<212> TYPE: DNA
<213> ORGANISM: Artificial Sequence
<220> FEATURE:
<223> OTHER INFORMATION: synthetic reverse amplification primer for
      target region containing SNP S70

<400> SEQUENCE: 34
cggccaccca tcctggagat                                                    20

<210> SEQ ID NO 35
<211> LENGTH: 21
<212> TYPE: DNA
<213> ORGANISM: Artificial Sequence
<220> FEATURE:
<223> OTHER INFORMATION: synthetic forward amplification primer for
      target region containing SNP S77

<400> SEQUENCE: 35
gggcctcagt tctagacgag t                                                  21

<210> SEQ ID NO 36
<211> LENGTH: 20
<212> TYPE: DNA
<213> ORGANISM: Artificial Sequence
<220> FEATURE:
<223> OTHER INFORMATION: synthetic reverse amplification primer for
      target region containing SNP S77

<400> SEQUENCE: 36
gtttccgtga agtaggcgct                                                    20

<210> SEQ ID NO 37
<211> LENGTH: 22
<212> TYPE: DNA
<213> ORGANISM: Artificial Sequence
<220> FEATURE:
<223> OTHER INFORMATION: synthetic forward amplification primer for
      target region containing SNP S78

<400> SEQUENCE: 37
aggcagaact aaacgttggc tt                                                 22

<210> SEQ ID NO 38
<211> LENGTH: 23
<212> TYPE: DNA
<213> ORGANISM: Artificial Sequence
```

```
<220> FEATURE:
<223> OTHER INFORMATION: synthetic reverse amplification primer for
      target region containing SNP S78

<400> SEQUENCE: 38
tgcggaacag tgacaatttg ttc                                              23

<210> SEQ ID NO 39
<211> LENGTH: 22
<212> TYPE: DNA
<213> ORGANISM: Artificial Sequence
<220> FEATURE:
<223> OTHER INFORMATION: synthetic forward amplification primer for
      target region containing SNP S79

<400> SEQUENCE: 39
cagggagtgc tttactgagg ca                                               22

<210> SEQ ID NO 40
<211> LENGTH: 20
<212> TYPE: DNA
<213> ORGANISM: Artificial Sequence
<220> FEATURE:
<223> OTHER INFORMATION: synthetic reverse amplification primer for
      target region containing SNP S79

<400> SEQUENCE: 40
actcaaacac ggagctgggc                                                  20

<210> SEQ ID NO 41
<211> LENGTH: 23
<212> TYPE: DNA
<213> ORGANISM: Artificial Sequence
<220> FEATURE:
<223> OTHER INFORMATION: synthetic forward amplification primer for
      target region containing SNP S80

<400> SEQUENCE: 41
aacttagctg ctcttgcttc agt                                              23

<210> SEQ ID NO 42
<211> LENGTH: 27
<212> TYPE: DNA
<213> ORGANISM: Artificial Sequence
<220> FEATURE:
<223> OTHER INFORMATION: synthetic reverse amplification primer for
      target region containing SNP S80

<400> SEQUENCE: 42
gtacctgcct taactcagta tgatctt                                          27

<210> SEQ ID NO 43
<211> LENGTH: 20
<212> TYPE: DNA
<213> ORGANISM: Artificial Sequence
<220> FEATURE:
<223> OTHER INFORMATION: synthetic forward amplification primer for
      target region containing SNP S82

<400> SEQUENCE: 43
tttgcacttg acgcaccagc                                                  20

<210> SEQ ID NO 44
<211> LENGTH: 21
<212> TYPE: DNA
<213> ORGANISM: Artificial Sequence
<220> FEATURE:
```

```
<223> OTHER INFORMATION: synthetic reverse amplification primer for
      target region containing SNP S82

<400> SEQUENCE: 44
ccgaggcaga ggaaggaagt g                                              21

<210> SEQ ID NO 45
<211> LENGTH: 24
<212> TYPE: DNA
<213> ORGANISM: Artificial Sequence
<220> FEATURE:
<223> OTHER INFORMATION: synthetic forward amplification primer for
      target region containing SNP S83

<400> SEQUENCE: 45
ggttttgctt ctgatgatcc ctct                                           24

<210> SEQ ID NO 46
<211> LENGTH: 25
<212> TYPE: DNA
<213> ORGANISM: Artificial Sequence
<220> FEATURE:
<223> OTHER INFORMATION: synthetic reverse amplification primer for
      target region containing SNP S83

<400> SEQUENCE: 46
agcattgtgt agggactggt aaatt                                          25

<210> SEQ ID NO 47
<211> LENGTH: 27
<212> TYPE: DNA
<213> ORGANISM: Artificial Sequence
<220> FEATURE:
<223> OTHER INFORMATION: synthetic forward amplification primer for
      target region containing SNP S84

<400> SEQUENCE: 47
ccccaaacta agtacctaat cactcgt                                        27

<210> SEQ ID NO 48
<211> LENGTH: 20
<212> TYPE: DNA
<213> ORGANISM: Artificial Sequence
<220> FEATURE:
<223> OTHER INFORMATION: synthetic reverse amplification primer for
      target region containing SNP S84

<400> SEQUENCE: 48
ccaaggggag catccaccat                                                20

<210> SEQ ID NO 49
<211> LENGTH: 21
<212> TYPE: DNA
<213> ORGANISM: Artificial Sequence
<220> FEATURE:
<223> OTHER INFORMATION: synthetic forward amplification primer for
      target region containing SNP S85

<400> SEQUENCE: 49
acacacacac acgcaattcg g                                              21

<210> SEQ ID NO 50
<211> LENGTH: 20
<212> TYPE: DNA
<213> ORGANISM: Artificial Sequence
<220> FEATURE:
<223> OTHER INFORMATION: synthetic reverse amplification primer for
``` target region containing SNP S85

<400> SEQUENCE: 50
atgagctgag gtgggtgctg                                              20

<210> SEQ ID NO 51
<211> LENGTH: 20
<212> TYPE: DNA
<213> ORGANISM: Artificial Sequence
<220> FEATURE:
<223> OTHER INFORMATION: synthetic forward amplification primer for
      target region containing SNP S86

<400> SEQUENCE: 51
gtctccctcc ccaaaggtgc                                              20

<210> SEQ ID NO 52
<211> LENGTH: 20
<212> TYPE: DNA
<213> ORGANISM: Artificial Sequence
<220> FEATURE:
<223> OTHER INFORMATION: synthetic reverse amplification primer for
      target region containing SNP S86

<400> SEQUENCE: 52
gccaacctca aggggcagtt                                              20

<210> SEQ ID NO 53
<211> LENGTH: 24
<212> TYPE: DNA
<213> ORGANISM: Artificial Sequence
<220> FEATURE:
<223> OTHER INFORMATION: synthetic forward amplification primer for
      target region containing SNP S87

<400> SEQUENCE: 53
ggcatctgaa ttcaagcttt ggtc                                         24

<210> SEQ ID NO 54
<211> LENGTH: 24
<212> TYPE: DNA
<213> ORGANISM: Artificial Sequence
<220> FEATURE:
<223> OTHER INFORMATION: synthetic reverse amplification primer for
      target region containing SNP S87

<400> SEQUENCE: 54
ttcttctagt tggtctggta ggct                                         24

<210> SEQ ID NO 55
<211> LENGTH: 25
<212> TYPE: DNA
<213> ORGANISM: Artificial Sequence
<220> FEATURE:
<223> OTHER INFORMATION: synthetic forward amplification primer for
      target region containing SNP S88

<400> SEQUENCE: 55
tggttattgt tactaggtcc ccacc                                        25

<210> SEQ ID NO 56
<211> LENGTH: 26
<212> TYPE: DNA
<213> ORGANISM: Artificial Sequence
<220> FEATURE:
<223> OTHER INFORMATION: synthetic reverse amplification primer for
      target region containing SNP S88

```
<400> SEQUENCE: 56
agaataagca agatgttggc agtgag                                          26

<210> SEQ ID NO 57
<211> LENGTH: 22
<212> TYPE: DNA
<213> ORGANISM: Artificial Sequence
<220> FEATURE:
<223> OTHER INFORMATION: synthetic forward amplification primer for
      target region containing SNP S90

<400> SEQUENCE: 57
tggttgaacg tccacagaag ga                                              22

<210> SEQ ID NO 58
<211> LENGTH: 19
<212> TYPE: DNA
<213> ORGANISM: Artificial Sequence
<220> FEATURE:
<223> OTHER INFORMATION: synthetic reverse amplification primer for
      target region containing SNP S90

<400> SEQUENCE: 58
caagcacacg tggctgctc                                                  19

<210> SEQ ID NO 59
<211> LENGTH: 21
<212> TYPE: DNA
<213> ORGANISM: Artificial Sequence
<220> FEATURE:
<223> OTHER INFORMATION: synthetic forward amplification primer for
      target region containing SNP S91

<400> SEQUENCE: 59
gcagagggaa gagaagaggc a                                               21

<210> SEQ ID NO 60
<211> LENGTH: 25
<212> TYPE: DNA
<213> ORGANISM: Artificial Sequence
<220> FEATURE:
<223> OTHER INFORMATION: synthetic reverse amplification primer for
      target region containing SNP S91

<400> SEQUENCE: 60
gcagtagata actctggctt tcagc                                           25

<210> SEQ ID NO 61
<211> LENGTH: 23
<212> TYPE: DNA
<213> ORGANISM: Artificial Sequence
<220> FEATURE:
<223> OTHER INFORMATION: synthetic forward amplification primer for
      target region containing SNP S92

<400> SEQUENCE: 61
gtgagcagaa tccaagcttc agc                                             23

<210> SEQ ID NO 62
<211> LENGTH: 22
<212> TYPE: DNA
<213> ORGANISM: Artificial Sequence
<220> FEATURE:
<223> OTHER INFORMATION: synthetic reverse amplification primer for
      target region containing SNP S92
```

```
<400> SEQUENCE: 62
ccccaccctc ataacaaccc tc                                        22

<210> SEQ ID NO 63
<211> LENGTH: 20
<212> TYPE: DNA
<213> ORGANISM: Artificial Sequence
<220> FEATURE:
<223> OTHER INFORMATION: synthetic forward amplification primer for
      target region containing SNP S94

<400> SEQUENCE: 63
ctggggcaga gtggagagtc                                           20

<210> SEQ ID NO 64
<211> LENGTH: 20
<212> TYPE: DNA
<213> ORGANISM: Artificial Sequence
<220> FEATURE:
<223> OTHER INFORMATION: synthetic reverse amplification primer for
      target region containing SNP S94

<400> SEQUENCE: 64
atccacctct gaacccagcc                                           20

<210> SEQ ID NO 65
<211> LENGTH: 20
<212> TYPE: DNA
<213> ORGANISM: Artificial Sequence
<220> FEATURE:
<223> OTHER INFORMATION: synthetic forward amplification primer for
      target region containing SNP S96

<400> SEQUENCE: 65
tcccaggctc caggtcagat                                           20

<210> SEQ ID NO 66
<211> LENGTH: 21
<212> TYPE: DNA
<213> ORGANISM: Artificial Sequence
<220> FEATURE:
<223> OTHER INFORMATION: synthetic reverse amplification primer for
      target region containing SNP S96

<400> SEQUENCE: 66
ggatcaatgt ggctgctccc t                                         21

<210> SEQ ID NO 67
<211> LENGTH: 21
<212> TYPE: DNA
<213> ORGANISM: Artificial Sequence
<220> FEATURE:
<223> OTHER INFORMATION: synthetic forward amplification primer for
      target region containing SNP S97

<400> SEQUENCE: 67
agccctgcac actcacttac c                                         21

<210> SEQ ID NO 68
<211> LENGTH: 24
<212> TYPE: DNA
<213> ORGANISM: Artificial Sequence
<220> FEATURE:
<223> OTHER INFORMATION: synthetic reverse amplification primer for
      target region containing SNP S97

<400> SEQUENCE: 68
```
tggcattcag atcatcaggc ttct                                         24

<210> SEQ ID NO 69
<211> LENGTH: 20
<212> TYPE: DNA
<213> ORGANISM: Artificial Sequence
<220> FEATURE:
<223> OTHER INFORMATION: synthetic forward amplification primer for
      target region containing SNP S99

<400> SEQUENCE: 69
ggcaaagtgg gcaagggtct                                              20

<210> SEQ ID NO 70
<211> LENGTH: 22
<212> TYPE: DNA
<213> ORGANISM: Artificial Sequence
<220> FEATURE:
<223> OTHER INFORMATION: synthetic reverse amplification primer for
      target region containing SNP S99

<400> SEQUENCE: 70
gcctcctaaa gcttgagcca ca                                           22

<210> SEQ ID NO 71
<211> LENGTH: 20
<212> TYPE: DNA
<213> ORGANISM: Artificial Sequence
<220> FEATURE:
<223> OTHER INFORMATION: synthetic forward amplification primer for
      target region containing SNP S102

<400> SEQUENCE: 71
aacagtggca gccctcttgt                                              20

<210> SEQ ID NO 72
<211> LENGTH: 22
<212> TYPE: DNA
<213> ORGANISM: Artificial Sequence
<220> FEATURE:
<223> OTHER INFORMATION: synthetic reverse amplification primer for
      target region containing SNP S102

<400> SEQUENCE: 72
acacttggtt catggggttg tg                                           22

<210> SEQ ID NO 73
<211> LENGTH: 21
<212> TYPE: DNA
<213> ORGANISM: Artificial Sequence
<220> FEATURE:
<223> OTHER INFORMATION: synthetic forward amplification primer for
      target region containing SNP S103

<400> SEQUENCE: 73
agctttcttg cttctgcccc a                                            21

<210> SEQ ID NO 74
<211> LENGTH: 20
<212> TYPE: DNA
<213> ORGANISM: Artificial Sequence
<220> FEATURE:
<223> OTHER INFORMATION: synthetic reverse amplification primer for
      target region containing SNP S103

<400> SEQUENCE: 74

```
gggtgccatt gcccagagat                                              20

<210> SEQ ID NO 75
<211> LENGTH: 22
<212> TYPE: DNA
<213> ORGANISM: Artificial Sequence
<220> FEATURE:
<223> OTHER INFORMATION: synthetic forward amplification primer for
      target region containing SNP S105

<400> SEQUENCE: 75
accccaagag gctttatagg gg                                           22

<210> SEQ ID NO 76
<211> LENGTH: 20
<212> TYPE: DNA
<213> ORGANISM: Artificial Sequence
<220> FEATURE:
<223> OTHER INFORMATION: synthetic reverse amplification primer for
      target region containing SNP S105

<400> SEQUENCE: 76
ccttcccaac gggtttgacc                                              20

<210> SEQ ID NO 77
<211> LENGTH: 20
<212> TYPE: DNA
<213> ORGANISM: Artificial Sequence
<220> FEATURE:
<223> OTHER INFORMATION: synthetic forward amplification primer for
      target region containing SNP S107

<400> SEQUENCE: 77
cttcccttgc ccctcttcca                                              20

<210> SEQ ID NO 78
<211> LENGTH: 20
<212> TYPE: DNA
<213> ORGANISM: Artificial Sequence
<220> FEATURE:
<223> OTHER INFORMATION: synthetic reverse amplification primer for
      target region containing SNP S107

<400> SEQUENCE: 78
tgctctgtgg atccctggag                                              20

<210> SEQ ID NO 79
<211> LENGTH: 20
<212> TYPE: DNA
<213> ORGANISM: Artificial Sequence
<220> FEATURE:
<223> OTHER INFORMATION: synthetic forward amplification primer for
      target region containing SNP S108

<400> SEQUENCE: 79
acactcctgc tgcgtgtctg                                              20

<210> SEQ ID NO 80
<211> LENGTH: 20
<212> TYPE: DNA
<213> ORGANISM: Artificial Sequence
<220> FEATURE:
<223> OTHER INFORMATION: synthetic reverse amplification primer for
      target region containing SNP S108

<400> SEQUENCE: 80
ttcctcccca ccactcccat                                              20
```

<210> SEQ ID NO 81
<211> LENGTH: 20
<212> TYPE: DNA
<213> ORGANISM: Artificial Sequence
<220> FEATURE:
<223> OTHER INFORMATION: synthetic forward amplification primer for
      target region containing SNP S110

<400> SEQUENCE: 81
ggtcctaccg aggtgggtga                                              20

<210> SEQ ID NO 82
<211> LENGTH: 22
<212> TYPE: DNA
<213> ORGANISM: Artificial Sequence
<220> FEATURE:
<223> OTHER INFORMATION: synthetic reverse amplification primer for
      target region containing SNP S110

<400> SEQUENCE: 82
cattgccaag gacagaggga ga                                           22

<210> SEQ ID NO 83
<211> LENGTH: 19
<212> TYPE: DNA
<213> ORGANISM: Artificial Sequence
<220> FEATURE:
<223> OTHER INFORMATION: synthetic SNP Probe A* for target region
      containing SNP S43

<400> SEQUENCE: 83
tggagacggg tccgcagag                                               19

<210> SEQ ID NO 84
<211> LENGTH: 19
<212> TYPE: DNA
<213> ORGANISM: Artificial Sequence
<220> FEATURE:
<223> OTHER INFORMATION: synthetic SNP Probe B* for target region
      containing SNP S43

<400> SEQUENCE: 84
tggcacaggt gctctccgg                                               19

<210> SEQ ID NO 85
<211> LENGTH: 25
<212> TYPE: DNA
<213> ORGANISM: Artificial Sequence
<220> FEATURE:
<223> OTHER INFORMATION: synthetic SNP Probe A* for target region
      containing SNP S46

<400> SEQUENCE: 85
ctgggagaga aagaacaaac agcat                                        25

<210> SEQ ID NO 86
<211> LENGTH: 25
<212> TYPE: DNA
<213> ORGANISM: Artificial Sequence
<220> FEATURE:
<223> OTHER INFORMATION: synthetic SNP Probe B* for target region
      containing SNP S46

<400> SEQUENCE: 86
catttcccca aatgctcttt gttct                                        25

```
<210> SEQ ID NO 87
<211> LENGTH: 22
<212> TYPE: DNA
<213> ORGANISM: Artificial Sequence
<220> FEATURE:
<223> OTHER INFORMATION: synthetic SNP Probe A* for target region
      containing SNP S38

<400> SEQUENCE: 87
aaaagggggt ggtgtcaatg tc                                              22

<210> SEQ ID NO 88
<211> LENGTH: 22
<212> TYPE: DNA
<213> ORGANISM: Artificial Sequence
<220> FEATURE:
<223> OTHER INFORMATION: synthetic SNP Probe B* for target region
      containing SNP S38

<400> SEQUENCE: 88
agggactgac attcacacca cc                                              22

<210> SEQ ID NO 89
<211> LENGTH: 18
<212> TYPE: DNA
<213> ORGANISM: Artificial Sequence
<220> FEATURE:
<223> OTHER INFORMATION: synthetic SNP Probe A* for target region
      containing SNP S48

<400> SEQUENCE: 89
cgggagccct gcgctttg                                                   18

<210> SEQ ID NO 90
<211> LENGTH: 21
<212> TYPE: DNA
<213> ORGANISM: Artificial Sequence
<220> FEATURE:
<223> OTHER INFORMATION: synthetic SNP Probe B* for target region
      containing SNP S48

<400> SEQUENCE: 90
tttccatgac aaaccgcagg g                                               21

<210> SEQ ID NO 91
<211> LENGTH: 19
<212> TYPE: DNA
<213> ORGANISM: Artificial Sequence
<220> FEATURE:
<223> OTHER INFORMATION: synthetic SNP Probe A* for target region
      containing SNP S50

<400> SEQUENCE: 91
cggttttcgc tcccgtgaa                                                  19

<210> SEQ ID NO 92
<211> LENGTH: 19
<212> TYPE: DNA
<213> ORGANISM: Artificial Sequence
<220> FEATURE:
<223> OTHER INFORMATION: synthetic SNP Probe B* for target region
      containing SNP S50

<400> SEQUENCE: 92
agtccatttc acgcgagcg                                                  19
```

<210> SEQ ID NO 93
<211> LENGTH: 25
<212> TYPE: DNA
<213> ORGANISM: Artificial Sequence
<220> FEATURE:
<223> OTHER INFORMATION: synthetic SNP Probe A* for target region containing SNP S51

<400> SEQUENCE: 93
ctttagctgc caagaaggat cagag                                          25

<210> SEQ ID NO 94
<211> LENGTH: 26
<212> TYPE: DNA
<213> ORGANISM: Artificial Sequence
<220> FEATURE:
<223> OTHER INFORMATION: synthetic SNP Probe B* for target region containing SNP S51

<400> SEQUENCE: 94
agaatgtgtg ttctcactct catcct                                         26

<210> SEQ ID NO 95
<211> LENGTH: 18
<212> TYPE: DNA
<213> ORGANISM: Artificial Sequence
<220> FEATURE:
<223> OTHER INFORMATION: synthetic SNP Probe A* for target region containing SNP S53

<400> SEQUENCE: 95
aggcctgggt ggagaagt                                                  18

<210> SEQ ID NO 96
<211> LENGTH: 21
<212> TYPE: DNA
<213> ORGANISM: Artificial Sequence
<220> FEATURE:
<223> OTHER INFORMATION: synthetic SNP Probe B* for target region containing SNP S53

<400> SEQUENCE: 96
ccagcccttg tctcaaaagc c                                              21

<210> SEQ ID NO 97
<211> LENGTH: 25
<212> TYPE: DNA
<213> ORGANISM: Artificial Sequence
<220> FEATURE:
<223> OTHER INFORMATION: synthetic SNP Probe A* for target region containing SNP S54

<400> SEQUENCE: 97
atgaaaccaa gcagtactgt ggaat                                          25

<210> SEQ ID NO 98
<211> LENGTH: 24
<212> TYPE: DNA
<213> ORGANISM: Artificial Sequence
<220> FEATURE:
<223> OTHER INFORMATION: synthetic SNP Probe B* for target region containing SNP S54

<400> SEQUENCE: 98
accaacaaat tccacactac tgct                                           24

<210> SEQ ID NO 99

```
<211> LENGTH: 21
<212> TYPE: DNA
<213> ORGANISM: Artificial Sequence
<220> FEATURE:
<223> OTHER INFORMATION: synthetic SNP Probe A* for target region
      containing SNP S55

<400> SEQUENCE: 99
acttctcagc aacagcctgg a                                         21

<210> SEQ ID NO 100
<211> LENGTH: 23
<212> TYPE: DNA
<213> ORGANISM: Artificial Sequence
<220> FEATURE:
<223> OTHER INFORMATION: synthetic SNP Probe B* for target region
      containing SNP S55

<400> SEQUENCE: 100
ctctggaaat tcatccagcc tgt                                       23

<210> SEQ ID NO 101
<211> LENGTH: 26
<212> TYPE: DNA
<213> ORGANISM: Artificial Sequence
<220> FEATURE:
<223> OTHER INFORMATION: synthetic SNP Probe A* for target region
      containing SNP S57

<400> SEQUENCE: 101
cactcacgtt tgggatactt cgtttc                                    26

<210> SEQ ID NO 102
<211> LENGTH: 27
<212> TYPE: DNA
<213> ORGANISM: Artificial Sequence
<220> FEATURE:
<223> OTHER INFORMATION: synthetic SNP Probe B* for target region
      containing SNP S57

<400> SEQUENCE: 102
cccagtaagg aatggagaaa ccaagta                                   27

<210> SEQ ID NO 103
<211> LENGTH: 20
<212> TYPE: DNA
<213> ORGANISM: Artificial Sequence
<220> FEATURE:
<223> OTHER INFORMATION: synthetic SNP Probe A* for target region
      containing SNP S58

<400> SEQUENCE: 103
attacaggca tgagccaccg                                           20

<210> SEQ ID NO 104
<211> LENGTH: 18
<212> TYPE: DNA
<213> ORGANISM: Artificial Sequence
<220> FEATURE:
<223> OTHER INFORMATION: synthetic SNP Probe B* for target region
      containing SNP S58

<400> SEQUENCE: 104
caaggcacgg tgcctcat                                             18

<210> SEQ ID NO 105
<211> LENGTH: 27
```

```
<212> TYPE: DNA
<213> ORGANISM: Artificial Sequence
<220> FEATURE:
<223> OTHER INFORMATION: synthetic SNP Probe A* for target region
      containing SNP S59

<400> SEQUENCE: 105
attacatagc ttatcacttg cagagcc                                         27

<210> SEQ ID NO 106
<211> LENGTH: 21
<212> TYPE: DNA
<213> ORGANISM: Artificial Sequence
<220> FEATURE:
<223> OTHER INFORMATION: synthetic SNP Probe B* for target region
      containing SNP S59

<400> SEQUENCE: 106
actcctggct ctgcaactga t                                               21

<210> SEQ ID NO 107
<211> LENGTH: 23
<212> TYPE: DNA
<213> ORGANISM: Artificial Sequence
<220> FEATURE:
<223> OTHER INFORMATION: synthetic SNP Probe A* for target region
      containing SNP S63

<400> SEQUENCE: 107
aactggaagt aacacctgca cca                                             23

<210> SEQ ID NO 108
<211> LENGTH: 21
<212> TYPE: DNA
<213> ORGANISM: Artificial Sequence
<220> FEATURE:
<223> OTHER INFORMATION: synthetic SNP Probe B* for target region
      containing SNP S63

<400> SEQUENCE: 108
cttgactctt ggtgcacgtg t                                               21

<210> SEQ ID NO 109
<211> LENGTH: 27
<212> TYPE: DNA
<213> ORGANISM: Artificial Sequence
<220> FEATURE:
<223> OTHER INFORMATION: synthetic SNP Probe A* for target region
      containing SNP S66

<400> SEQUENCE: 109
aggatattgc tagagtggag tcagaac                                         27

<210> SEQ ID NO 110
<211> LENGTH: 27
<212> TYPE: DNA
<213> ORGANISM: Artificial Sequence
<220> FEATURE:
<223> OTHER INFORMATION: synthetic SNP Probe B* for target region
      containing SNP S66

<400> SEQUENCE: 110
accactgtta tttgttctca ctccact                                         27

<210> SEQ ID NO 111
<211> LENGTH: 19
<212> TYPE: DNA
```

<213> ORGANISM: Artificial Sequence
<220> FEATURE:
<223> OTHER INFORMATION: synthetic SNP Probe A* for target region
      containing SNP S67

<400> SEQUENCE: 111
cccgaccctt aacctcccc                                              19

<210> SEQ ID NO 112
<211> LENGTH: 21
<212> TYPE: DNA
<213> ORGANISM: Artificial Sequence
<220> FEATURE:
<223> OTHER INFORMATION: synthetic SNP Probe B* for target region
      containing SNP S67

<400> SEQUENCE: 112
tggagagggt tggggacgtt a                                           21

<210> SEQ ID NO 113
<211> LENGTH: 23
<212> TYPE: DNA
<213> ORGANISM: Artificial Sequence
<220> FEATURE:
<223> OTHER INFORMATION: synthetic SNP Probe A* for target region
      containing SNP S68

<400> SEQUENCE: 113
agacacttgt gggactcaga agg                                         23

<210> SEQ ID NO 114
<211> LENGTH: 21
<212> TYPE: DNA
<213> ORGANISM: Artificial Sequence
<220> FEATURE:
<223> OTHER INFORMATION: synthetic SNP Probe B* for target region
      containing SNP S68

<400> SEQUENCE: 114
acaactgtct cctgctgtcc t                                           21

<210> SEQ ID NO 115
<211> LENGTH: 19
<212> TYPE: DNA
<213> ORGANISM: Artificial Sequence
<220> FEATURE:
<223> OTHER INFORMATION: synthetic SNP Probe A* for target region
      containing SNP S70

<400> SEQUENCE: 115
accctcctgt actgcgcac                                              19

<210> SEQ ID NO 116
<211> LENGTH: 20
<212> TYPE: DNA
<213> ORGANISM: Artificial Sequence
<220> FEATURE:
<223> OTHER INFORMATION: synthetic SNP Probe B* for target region
      containing SNP S70

<400> SEQUENCE: 116
acagtgaagg tgtgcccagt                                             20

<210> SEQ ID NO 117
<211> LENGTH: 19
<212> TYPE: DNA
<213> ORGANISM: Artificial Sequence

```
<220> FEATURE:
<223> OTHER INFORMATION: synthetic SNP Probe A* for target region
      containing SNP S77

<400> SEQUENCE: 117
atgctcagca cacagggga                                                    19

<210> SEQ ID NO 118
<211> LENGTH: 18
<212> TYPE: DNA
<213> ORGANISM: Artificial Sequence
<220> FEATURE:
<223> OTHER INFORMATION: synthetic SNP Probe B* for target region
      containing SNP S77

<400> SEQUENCE: 118
cactgcttcc cccgtgtg                                                     18

<210> SEQ ID NO 119
<211> LENGTH: 20
<212> TYPE: DNA
<213> ORGANISM: Artificial Sequence
<220> FEATURE:
<223> OTHER INFORMATION: synthetic SNP Probe A* for target region
      containing SNP S78

<400> SEQUENCE: 119
atgcagcttt ggcatgaggt                                                   20

<210> SEQ ID NO 120
<211> LENGTH: 24
<212> TYPE: DNA
<213> ORGANISM: Artificial Sequence
<220> FEATURE:
<223> OTHER INFORMATION: synthetic SNP Probe B* for target region
      containing SNP S78

<400> SEQUENCE: 120
atgccaaagc cgcatatttt ctct                                              24

<210> SEQ ID NO 121
<211> LENGTH: 18
<212> TYPE: DNA
<213> ORGANISM: Artificial Sequence
<220> FEATURE:
<223> OTHER INFORMATION: synthetic SNP Probe A* for target region
      containing SNP S79

<400> SEQUENCE: 121
ggcagcaggt gccaagca                                                     18

<210> SEQ ID NO 122
<211> LENGTH: 20
<212> TYPE: DNA
<213> ORGANISM: Artificial Sequence
<220> FEATURE:
<223> OTHER INFORMATION: synthetic SNP Probe B* for target region
      containing SNP S79

<400> SEQUENCE: 122
aggcattact gctcggcacc                                                   20

<210> SEQ ID NO 123
<211> LENGTH: 19
<212> TYPE: DNA
<213> ORGANISM: Artificial Sequence
<220> FEATURE:
```

<223> OTHER INFORMATION: synthetic SNP Probe A* for target region
      containing SNP S80

<400> SEQUENCE: 123
cccagcagga aagcgagtc                                                    19

<210> SEQ ID NO 124
<211> LENGTH: 24
<212> TYPE: DNA
<213> ORGANISM: Artificial Sequence
<220> FEATURE:
<223> OTHER INFORMATION: synthetic SNP Probe B* for target region
      containing SNP S80

<400> SEQUENCE: 124
aagtaagaat cagacccgct ttcc                                              24

<210> SEQ ID NO 125
<211> LENGTH: 20
<212> TYPE: DNA
<213> ORGANISM: Artificial Sequence
<220> FEATURE:
<223> OTHER INFORMATION: synthetic SNP Probe A* for target region
      containing SNP S82

<400> SEQUENCE: 125
tgcaatgaga gcagaggcct                                                   20

<210> SEQ ID NO 126
<211> LENGTH: 18
<212> TYPE: DNA
<213> ORGANISM: Artificial Sequence
<220> FEATURE:
<223> OTHER INFORMATION: synthetic SNP Probe B* for target region
      containing SNP S82

<400> SEQUENCE: 126
catcgcagcc ctcctgca                                                     18

<210> SEQ ID NO 127
<211> LENGTH: 24
<212> TYPE: DNA
<213> ORGANISM: Artificial Sequence
<220> FEATURE:
<223> OTHER INFORMATION: synthetic SNP Probe A* for target region
      containing SNP S83

<400> SEQUENCE: 127
atacactctg ttgttgagtg ccac                                              24

<210> SEQ ID NO 128
<211> LENGTH: 26
<212> TYPE: DNA
<213> ORGANISM: Artificial Sequence
<220> FEATURE:
<223> OTHER INFORMATION: synthetic SNP Probe B* for target region
      containing SNP S83

<400> SEQUENCE: 128
cagagcgtat gtatgaagtc cagagt                                            26

<210> SEQ ID NO 129
<211> LENGTH: 21
<212> TYPE: DNA
<213> ORGANISM: Artificial Sequence
<220> FEATURE:
<223> OTHER INFORMATION: synthetic SNP Probe A* for target region -continued containing SNP S84

<400> SEQUENCE: 129
cccacgggag gaatgtcttt g                                   21

<210> SEQ ID NO 130
<211> LENGTH: 18
<212> TYPE: DNA
<213> ORGANISM: Artificial Sequence
<220> FEATURE:
<223> OTHER INFORMATION: synthetic SNP Probe B* for target region
      containing SNP S84

<400> SEQUENCE: 130
cccatgggac ttctggcc                                       18

<210> SEQ ID NO 131
<211> LENGTH: 18
<212> TYPE: DNA
<213> ORGANISM: Artificial Sequence
<220> FEATURE:
<223> OTHER INFORMATION: synthetic SNP Probe A* for target region
      containing SNP S85

<400> SEQUENCE: 131
acacaaagtg gcctcccg                                       18

<210> SEQ ID NO 132
<211> LENGTH: 18
<212> TYPE: DNA
<213> ORGANISM: Artificial Sequence
<220> FEATURE:
<223> OTHER INFORMATION: synthetic SNP Probe B* for target region
      containing SNP S85

<400> SEQUENCE: 132
acagagtggc ctcccgat                                       18

<210> SEQ ID NO 133
<211> LENGTH: 26
<212> TYPE: DNA
<213> ORGANISM: Artificial Sequence
<220> FEATURE:
<223> OTHER INFORMATION: synthetic SNP Probe A* for target region
      containing SNP S86

<400> SEQUENCE: 133
aggaaagaaa cctttcagat gtcagt                              26

<210> SEQ ID NO 134
<211> LENGTH: 26
<212> TYPE: DNA
<213> ORGANISM: Artificial Sequence
<220> FEATURE:
<223> OTHER INFORMATION: synthetic SNP Probe B* for target region
      containing SNP S86

<400> SEQUENCE: 134
tgaggattaa ctgacatccg aaaggt                              26

<210> SEQ ID NO 135
<211> LENGTH: 20
<212> TYPE: DNA
<213> ORGANISM: Artificial Sequence
<220> FEATURE:
<223> OTHER INFORMATION: synthetic SNP Probe A* for target region
      containing SNP S87

-continued

<210> SEQ ID NO 135
<400> SEQUENCE: 135
aggcttgtac actctccccc                                              20

<210> SEQ ID NO 136
<211> LENGTH: 20
<212> TYPE: DNA
<213> ORGANISM: Artificial Sequence
<220> FEATURE:
<223> OTHER INFORMATION: synthetic SNP Probe B* for target region
      containing SNP S87

<400> SEQUENCE: 136
acactgggat gggggaaagt                                              20

<210> SEQ ID NO 137
<211> LENGTH: 23
<212> TYPE: DNA
<213> ORGANISM: Artificial Sequence
<220> FEATURE:
<223> OTHER INFORMATION: synthetic SNP Probe A* for target region
      containing SNP S88

<400> SEQUENCE: 137
aggactttat tggggaggct gac                                          23

<210> SEQ ID NO 138
<211> LENGTH: 21
<212> TYPE: DNA
<213> ORGANISM: Artificial Sequence
<220> FEATURE:
<223> OTHER INFORMATION: synthetic SNP Probe B* for target region
      containing SNP S88

<400> SEQUENCE: 138
ctggaagcca aagtcaccct c                                            21

<210> SEQ ID NO 139
<211> LENGTH: 19
<212> TYPE: DNA
<213> ORGANISM: Artificial Sequence
<220> FEATURE:
<223> OTHER INFORMATION: synthetic SNP Probe A* for target region
      containing SNP S90

<400> SEQUENCE: 139
cagtgccctc tgccaggaa                                               19

<210> SEQ ID NO 140
<211> LENGTH: 19
<212> TYPE: DNA
<213> ORGANISM: Artificial Sequence
<220> FEATURE:
<223> OTHER INFORMATION: synthetic SNP Probe B* for target region
      containing SNP S90

<400> SEQUENCE: 140
gggccctgcc tgagcatag                                               19

<210> SEQ ID NO 141
<211> LENGTH: 23
<212> TYPE: DNA
<213> ORGANISM: Artificial Sequence
<220> FEATURE:
<223> OTHER INFORMATION: synthetic SNP Probe A* for target region
      containing SNP S91

```
<400> SEQUENCE: 141
cctcctcccc ccaaaatttt agt                                              23

<210> SEQ ID NO 142
<211> LENGTH: 19
<212> TYPE: DNA
<213> ORGANISM: Artificial Sequence
<220> FEATURE:
<223> OTHER INFORMATION: synthetic SNP Probe B* for target region
      containing SNP S91

<400> SEQUENCE: 142
tggggtgagg aggactgga                                                   19

<210> SEQ ID NO 143
<211> LENGTH: 19
<212> TYPE: DNA
<213> ORGANISM: Artificial Sequence
<220> FEATURE:
<223> OTHER INFORMATION: synthetic SNP Probe A* for target region
      containing SNP S92

<400> SEQUENCE: 143
cccgcagttg cacagcttg                                                   19

<210> SEQ ID NO 144
<211> LENGTH: 18
<212> TYPE: DNA
<213> ORGANISM: Artificial Sequence
<220> FEATURE:
<223> OTHER INFORMATION: synthetic SNP Probe B* for target region
      containing SNP S92

<400> SEQUENCE: 144
actgcaggcc acaaggtg                                                    18

<210> SEQ ID NO 145
<211> LENGTH: 18
<212> TYPE: DNA
<213> ORGANISM: Artificial Sequence
<220> FEATURE:
<223> OTHER INFORMATION: synthetic SNP Probe A* for target region
      containing SNP S94

<400> SEQUENCE: 145
aggacactgc agctgtgg                                                    18

<210> SEQ ID NO 146
<211> LENGTH: 20
<212> TYPE: DNA
<213> ORGANISM: Artificial Sequence
<220> FEATURE:
<223> OTHER INFORMATION: synthetic SNP Probe B* for target region
      containing SNP S94

<400> SEQUENCE: 146
cagcgtcctc tgtgctacct                                                  20

<210> SEQ ID NO 147
<211> LENGTH: 20
<212> TYPE: DNA
<213> ORGANISM: Artificial Sequence
<220> FEATURE:
<223> OTHER INFORMATION: synthetic SNP Probe A* for target region
      containing SNP S96

<400> SEQUENCE: 147
```
tctccgccct tctgagatgc                                              20

<210> SEQ ID NO 148
<211> LENGTH: 20
<212> TYPE: DNA
<213> ORGANISM: Artificial Sequence
<220> FEATURE:
<223> OTHER INFORMATION: synthetic SNP Probe B* for target region
      containing SNP S96

<400> SEQUENCE: 148
agggcagaga ctctggaact                                              20

<210> SEQ ID NO 149
<211> LENGTH: 19
<212> TYPE: DNA
<213> ORGANISM: Artificial Sequence
<220> FEATURE:
<223> OTHER INFORMATION: synthetic SNP Probe A* for target region
      containing SNP S97

<400> SEQUENCE: 149
ccatcaggtg ctggcactc                                               19

<210> SEQ ID NO 150
<211> LENGTH: 18
<212> TYPE: DNA
<213> ORGANISM: Artificial Sequence
<220> FEATURE:
<223> OTHER INFORMATION: synthetic SNP Probe B* for target region
      containing SNP S97

<400> SEQUENCE: 150
tgcagggaag agcgccag                                                18

<210> SEQ ID NO 151
<211> LENGTH: 18
<212> TYPE: DNA
<213> ORGANISM: Artificial Sequence
<220> FEATURE:
<223> OTHER INFORMATION: synthetic SNP Probe A* for target region
      containing SNP S99

<400> SEQUENCE: 151
ttggggccag gtacctgg                                                18

<210> SEQ ID NO 152
<211> LENGTH: 18
<212> TYPE: DNA
<213> ORGANISM: Artificial Sequence
<220> FEATURE:
<223> OTHER INFORMATION: synthetic SNP Probe B* for target region
      containing SNP S99

<400> SEQUENCE: 152
tggggccaag tacctggt                                                18

<210> SEQ ID NO 153
<211> LENGTH: 25
<212> TYPE: DNA
<213> ORGANISM: Artificial Sequence
<220> FEATURE:
<223> OTHER INFORMATION: synthetic SNP Probe A* for target region
      containing SNP S102

<400> SEQUENCE: 153
tggccttatc tttggcccta acatg                                      25

<210> SEQ ID NO 154
<211> LENGTH: 23
<212> TYPE: DNA
<213> ORGANISM: Artificial Sequence
<220> FEATURE:
<223> OTHER INFORMATION: synthetic SNP Probe B* for target region
      containing SNP S102

<400> SEQUENCE: 154
aggcacatcc tacatcttag ggc                                        23

<210> SEQ ID NO 155
<211> LENGTH: 18
<212> TYPE: DNA
<213> ORGANISM: Artificial Sequence
<220> FEATURE:
<223> OTHER INFORMATION: synthetic SNP Probe A* for target region
      containing SNP S103

<400> SEQUENCE: 155
ccctggggcc atcaggtt                                              18

<210> SEQ ID NO 156
<211> LENGTH: 19
<212> TYPE: DNA
<213> ORGANISM: Artificial Sequence
<220> FEATURE:
<223> OTHER INFORMATION: synthetic SNP Probe B* for target region
      containing SNP S103

<400> SEQUENCE: 156
ccctggggcc atcaagttt                                             19

<210> SEQ ID NO 157
<211> LENGTH: 18
<212> TYPE: DNA
<213> ORGANISM: Artificial Sequence
<220> FEATURE:
<223> OTHER INFORMATION: synthetic SNP Probe A* for target region
      containing SNP S105

<400> SEQUENCE: 157
ccactgggct ggcccctc                                              18

<210> SEQ ID NO 158
<211> LENGTH: 18
<212> TYPE: DNA
<213> ORGANISM: Artificial Sequence
<220> FEATURE:
<223> OTHER INFORMATION: synthetic SNP Probe B* for target region
      containing SNP S105

<400> SEQUENCE: 158
agtggaggag ggaccagc                                              18

<210> SEQ ID NO 159
<211> LENGTH: 20
<212> TYPE: DNA
<213> ORGANISM: Artificial Sequence
<220> FEATURE:
<223> OTHER INFORMATION: synthetic SNP Probe A* for target region
      containing SNP S107

<400> SEQUENCE: 159
aggttgtgtg aaagtgccct                                            20

<210> SEQ ID NO 160
<211> LENGTH: 19
<212> TYPE: DNA
<213> ORGANISM: Artificial Sequence
<220> FEATURE:
<223> OTHER INFORMATION: synthetic SNP Probe B* for target region
      containing SNP S107

<400> SEQUENCE: 160
agccctcagg gcaccttca                                              19

<210> SEQ ID NO 161
<211> LENGTH: 18
<212> TYPE: DNA
<213> ORGANISM: Artificial Sequence
<220> FEATURE:
<223> OTHER INFORMATION: synthetic SNP Probe A* for target region
      containing SNP S108

<400> SEQUENCE: 161
ggtcccagct ggtcgtgg                                               18

<210> SEQ ID NO 162
<211> LENGTH: 19
<212> TYPE: DNA
<213> ORGANISM: Artificial Sequence
<220> FEATURE:
<223> OTHER INFORMATION: synthetic SNP Probe B* for target region
      containing SNP S108

<400> SEQUENCE: 162
atgctcccca caaccagct                                              19

<210> SEQ ID NO 163
<211> LENGTH: 24
<212> TYPE: DNA
<213> ORGANISM: Artificial Sequence
<220> FEATURE:
<223> OTHER INFORMATION: synthetic SNP Probe A* for target region
      containing SNP S110

<400> SEQUENCE: 163
tttggtaggg aaggaactcc caat                                        24

<210> SEQ ID NO 164
<211> LENGTH: 22
<212> TYPE: DNA
<213> ORGANISM: Artificial Sequence
<220> FEATURE:
<223> OTHER INFORMATION: synthetic SNP Probe B* for target region
      containing SNP S110

<400> SEQUENCE: 164
atcagtggcc attgtgagtt cc                                          22

DETECTION AND QUANTIFICATION OF DONOR CELL-FREE DNA IN THE CIRCULATION OF ORGAN TRANSPLANT RECIPIENTS

CROSS-REFERENCE TO RELATED APPLICATIONS

This application is a continuation of U.S. application Ser. No. 14/893,807, filed May 29, 2014, which is a National Stage of International Application No. PCT/US2014/040055, filed May 29, 2014, which claims priority benefit to U.S. provisional application No. 61/828,553, filed May 29, 2013, each of which applications is herein incorporated by reference.

REFERENCE TO SEQUENCE LISTING

This application includes a Sequence Listing as a text file named "083443_1080953_SEQ.txt" created Mar. 13, 2018, and containing 38,956 bytes. The material contained in this text file is incorporated by reference in its entirety for all purposes.

BACKGROUND OF THE INVENTION

Using modern molecular biological techniques the detection of trace amounts of divergent genetic material in a single sample is feasible. This has potential applications for a number of conditions such as prenatal diagnosis, tumor diagnosis, and detection of transplant rejection. An increase of heart donor DNA in the circulation of stable heart transplant recipients during rejection episodes has been reported (Snyder, et al., *Proc Natl Acad Sci USA* 108:6229-6234, 2011). However, to be clinically useful the method used for the detection of graft DNA must not only be specific and sensitive, it must also have a rapid turn-around-time and be economically feasible to perform. The methods described to date are extremely time consuming and expensive to perform (Lo, *Clin Chem* 57:941-942, 2011).

Simplified methods to differentiate between DNA from donors and recipients can involve the use of single-nucleotide-polymorphisms (SNPs). One possibility is to interrogate both donor and recipient for certain SNPs and use those, where both SNPs are homozygous, but different in donor and recipient. However, this would require DNA from the donor to be available, which isn't always the case in the clinical setting, in particular if the transplantation was some years before. There is thus a need for sensitive, easily implemented techniques for early detection of transplant rejection.

BRIEF SUMMARY OF THE INVENTION

Certain aspects of the invention are summarized below. The invention is not limited to the particular embodiments described in this summary.

In one aspect, the invention provides a method of detecting transplant rejection in a patient based on the use of SNPs that have been investigated for their minor allelic frequency (MAF) where such frequencies are 0.2 or higher. In some embodiments, the MAF is 0.40 or higher. For example, assuming Hardy-Weinberg equilibrium, a SNP with a MAF of ~0.40 would show homozygosis in both donor and recipient 23%-25% of the time for each allele. The probability of both having a different allele (homozygous) is therefore ~11.3% to ~12.5%. In order to identify at least three such SNPs in Caucasians 30 to 35 different SNPs with the mentioned characteristics can be interrogated. In contrast, if unselected SNPs were employed, it can be estimated that over 3,000 assays are needed to achieve the same discriminating power, based on the overall median MAF of 0.023 reported for known human SNPs in Caucasians (e.g. for the Illumina HumanOmni5M bead chip).

Using such SNP comparisons, the amount of graft DNA released by an organ into the circulation can be assessed and used as a biomarker for organ integrity. In addition, once SNPs that differ between donor and recipient are identified only SNPs with the best sensitivity (e.g., homozygous in both but different in donor and recipient) need to be measured subsequently. The only limitation of such a method is the amount of DNA that is interrogated, which is mainly driven by the volume of blood that is analyzed. For example, it can be estimated that the number of genome equivalents in one milliliter of blood is about one thousand. If all molecules take part in a PCR reaction and the graft DNA accounts for 5% of cfDNA then there would be 50 such molecules in 1 mL of blood. The entire analysis of several different SNPs, therefore, when working with small samples, entails as a first step the random unbiased amplification of extracted cfDNA coming from a blood sample, e.g., typically a sample of at least 2 mL of blood. Such an amplification step can be done by several techniques, for the usually short apoptotic cfDNA (e.g., Beck et al., *Clin Chem* 55:730-738, 2009) a direct adaptor ligation is often most suitable (Lo et al., *Sci Transl Med* 2: 61ra91, 2010). Once the amplification adaptors are ligated, a moderate number of amplification cycles are performed (generally not more than 12 to 15) and the resulting library is cleaned from primers and adaptors and used as template for the SNP interrogations. If the initial sample size is not limited to a small sample, the amplification step, which is also referred to herein as a pre-amplification step, may be omitted.

Thus, in one aspect, the invention provides a method of detecting a SNP from a donor to monitor transplant status of a recipient receiving tissue from said donor, the method comprising: (a) identifying a SNP having a minor allele frequency of 0.20 or greater, often 0.30 or greater, or preferably 0.40 or greater, as homozygous in the recipient; (b) amplifying cell-free (cfDNA) from a serum or plasma sample obtained from the recipient at least 5 days after transplantation of material from the donor to generate a cf library (c) performing a digital PCR reaction for the SNPs identified in (a) to detect the presence of an alternative allele for one or more of the SNPs, and (d) selecting a SNP where the alternative SNP allele is present in the cf library to monitor transplant status of the patient. Preferably, the SNP selected in (d) is homozygous in the donor, but may be heterozygous in the donor. Step (a) can be performed using any sample from the patient that would not contain donor material, for example, peripheral blood leukocytes (PBLs) obtained from the patient may be used to identify a suitable SNP. In alternative embodiments, step (a) is performed using the cfDNA library of step (b). Thus, in some embodiments, e.g., using a PBL sample from the patient to obtain DNA, step (a) may be performed before or after step (b) whereas in other embodiments, the amplified cfDNA library is generated first. In some embodiments, a suitable SNP to be evaluated for monitoring transplant status is a SNP set forth in Table 1. In some embodiments, at least 5, 10, 15, 20, 25, 30, 35, 40, or all of the SNPs set forth in Table 1 are evaluated to determine those SNPs that are homozygous in the recipient.

In another aspect, the invention provides a method of detecting a SNP from a donor to monitor transplant status of a recipient receiving tissue from said donor, the method comprising: (a) identifying that a SNP having a minor allele frequency of 0.20 or greater, often 0.30 or greater, or preferably 0.40 or greater, as homozygous in the recipient; (b) amplifying cell-free (cfDNA) from a blood sample, e.g., serum or plasma, obtained from the recipient 24 hours or less after transplantation of graft material from the donor to generate a cf library; (c) identifying a SNP having a minor allele frequency of 0.20 or greater, often 0.30 or greater, or preferably 0.40 or greater, as homozygous in the donor using the cf library of step (b); (d) performing a digital PCR reaction for the SNPs identified in (a) to detect the presence of the alternative allele for one or more of the SNPs in the donor, and (e) selecting a SNP where the alternative SNP allele is present in the donor. Step (a) can be performed using any sample from the patient that would not contain donor material, for example, peripheral blood leukocytes (PBLs) obtained from the patient may be used to identify a suitable SNP. In some embodiments, a suitable SNP is a SNP set forth in Table 1. In some embodiments, at least 5, 10, 15, 20, 25, 30, 35, 40, or all of the SNPs set forth in Table 1 are evaluated to determine those SNPs that are homozygous in the recipient.

In a further aspect, the invention provides a method of detecting a SNP from a donor to monitor transplant status of a recipient receiving tissue from said donor DNA, the method comprising: (a) identifying a SNP having a minor allele frequency of 0.20 or greater, often 0.30 or greater, or preferably 0.40 or greater, as homozygous in a recipient using a DNA sample from the recipient from a source that is free of donor DNA, e.g., DNA obtained from a PBL sample from the patient; (b) identifying a SNP having a minor allele frequency of 0.20 or greater, often 0.30 or greater, or preferably 0.40 or greater, as homozygous in a recipient using a DNA sample obtained from donor cells or tissue; and (c) selecting a SNP that is homozygous in the recipient for which the donor is homozygous or heterozygous for the alternative allele. In some embodiments, SNP genotype is determined in recipient and/or donor DNA for at least 10, 20, 30, or 40 of the SNPs identified in Table 1. In some embodiments, the SNP evaluation may employ one or more probes having a sequence as shown in Table 1. SNPs for which the transplant material has a different allele for the SNP compared to the recipient can then be used for future determination of graft cfDNA percentage, e.g., in a digital PCR reaction.

In a further aspect, the invention provides a method of monitoring transplant rejection in a transplant recipient, the method comprising: obtaining a cfDNA sample from the patient; and detecting the presence or absence, or quantifying, a donor SNP allele for a SNP selected using a method as described herein. In typical embodiments, cfDNA samples are obtained from the patient at desired time points following transplantation and the level of the donor SNP allele is quantified.

In a further aspect, the invention provides a method of monitoring the status of a transplant in a transplant recipient to evaluate immunosuppressive therapy where the method comprises quantifying the amount of the donor allele SNP at desired time points and adjusting the immunosuppressive therapy, e.g., adjusting the amount of immunosuppressive drug. Thus, the lowest dose of an immunosuppressive drug can be identified for that individual patient.

In a further aspect, the invention provides a method of monitoring the status of a transplant in a transplant recipient, e.g., a liver transplant recipient, to determine changes in the transplant status related to reactivation of a virus, such as a hepatitis virus, where the method comprises quantifying the amount of donor SNP allele as described herein present in the blood of a transplant recipient.

In a further aspect, the invention provides a method of monitoring the status of a transplant in a transplant recipient to evaluate reperfusion injury to the transplant. In such embodiments, the amounts of graft cfDNA (GcfDNA) are determined over a time course, for example, a time course of days or weeks up to a month following transplant. In typical embodiments, GcfDNA is monitored over the first 7 days after engraftment.

In another aspect, the invention provides a method of determining the status of a transplanted organ where the organ is a marginal organ, wherein the method comprises determining the level of graft cfDNA present in the blood of a patient. In some embodiments, the method comprises determining the level of graft cfDNA over a course of seven days, or up to 30 days following transplant.

In additional aspects, the invention provides a method of evaluating the transplant status of a transplant recipient, the method comprising monitoring the level of graft cfDNA by assessing the amount of a donor SNP allele in a cfDNA sample obtained from the blood of a patient, typically where the SNP has a MAF of at least 0.20 or at least 0.30, and often at least 0.40, wherein the donor SNP allele is present in the donor and the recipient is homozygous for an alternative allele. The donor may be heterozygous or homozygous for the SNP allele. In some embodiments, quantifying the level of the donor SNP allele in the cfDNA sample comprises determining copy number of the donor SNP allele in the cfDNA sample. In some embodiments quantifying the level of the donor SNP allele in the cfDNA sample comprises determining the percentage of the donor SNP allele in the cfDNA sample. In some embodiments, the transplanted material is a marginal organ. In some embodiments, the cfDNA sample is from a blood sample, e.g., serum or plasma, that is obtained ten days or longer following transplant. In some embodiments, the cfDNA sample is obtained from a blood sample e.g., serum or plasma, obtained a year or longer following transplant. In some embodiments, the cfDNA sample is from a blood sample, e.g., serum or plasma, that is obtained within seven days of transplant. In some embodiments, monitoring the level of graft cfDNA in accordance with the invention further comprises adjusting an administration schedule or dosage or of one or more immunosuppressive drugs. In some embodiments, the donor material is a liver, heart, or kidney. In some embodiments, monitoring the level of graft cfDNA can be performed to monitor transplant damage that may arise from donor-specific antibodies in the blood of the recipient. Thus, in some embodiments, a method of the invention may further comprise detecting donor-specific antibodies in the blood of the recipient.

In a further aspect, the invention further provides use of a method of monitoring graft cfDNA using a SNP assay as described herein to detect transplant damage from various causes, including, but not limited to, reperfusion damage to the organ in a transplant recipient, liver damage from a reactivated hepatitis virus in a liver transplant recipient, transplant damage from donor-specific antibodies, or damage from a chronic transplant injury, e.g., chronic nephropathy in a kidney transplant or vasculopathy in a heart transplant. In some embodiments, the method of monitoring graft cfDNA using a SNP assay as described herein is used for determining a minimal effective immunosuppressive regimen.

DETAILED DESCRIPTION OF THE INVENTION

Figure 1:
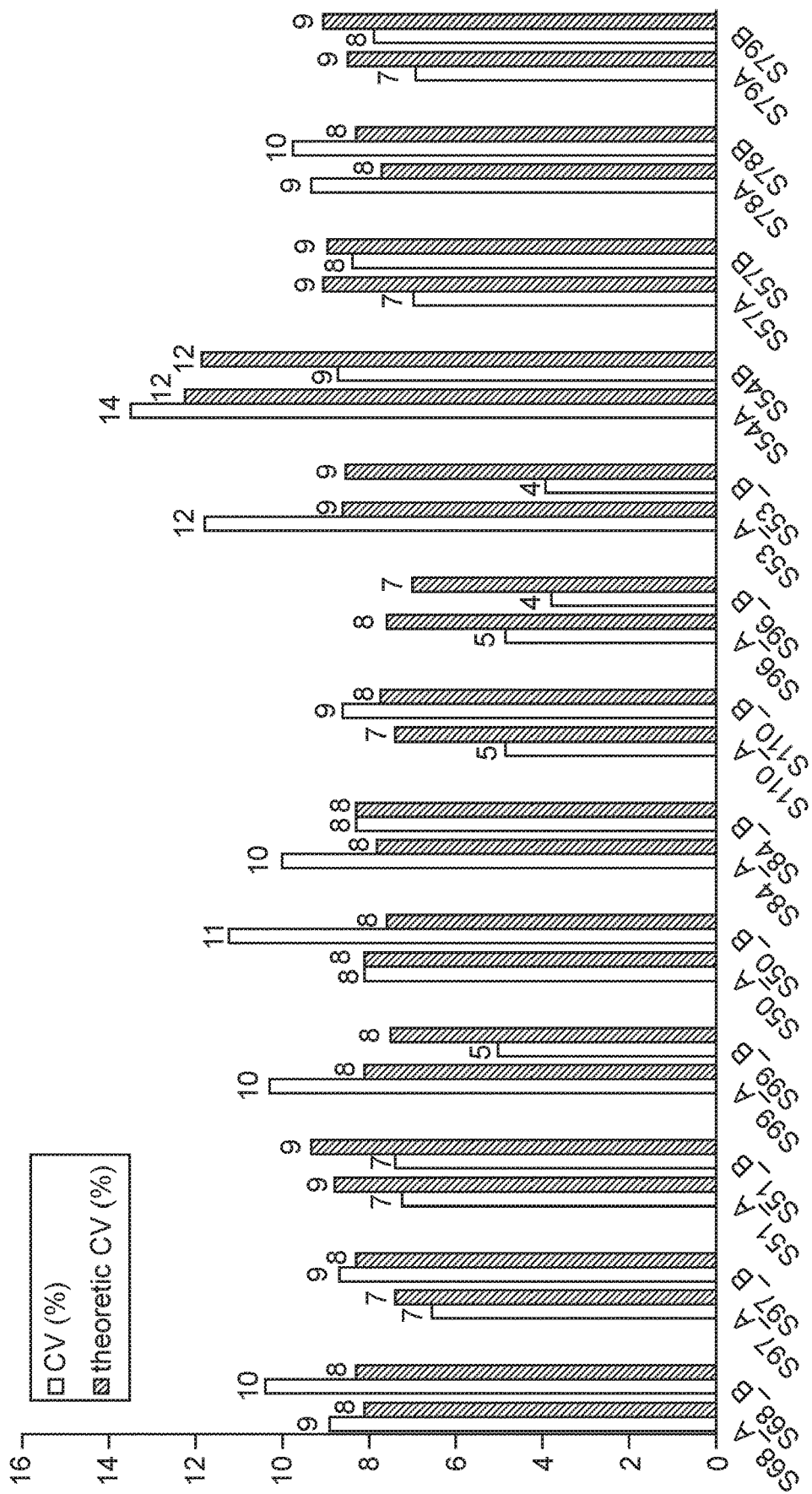
FIG. 1 provides a graph showing coefficients of variation (%) for 15 assays with 2% minor allele concentration. For each assay the CV for 2% allele A and 20/% allele B are shown (black bars). The intra-assay precision was obtained in 9 repetitions within in the same QX100 run using 100 ng total input DNA. Grey bars show the theoretical CVs as calculated from the number of droplets positive for the minor allele.

The term "cell-free DNA" or "cfDNA" as used herein means free DNA molecules of 25 nucleotides or longer that are not contained within any intact cells. In the context of the current invention, "cfDNA" is typically evaluated in human blood, e.g., can be obtained from human serum or plasma.

A "single nucleotide polymorphism (SNP) biomarker" in the context of this invention refers to a SNP where a recipient of a transplant is homozygous for one SNP allele and the donor has at least one alternative allele for that SNP. Such a SNP is a biomarker for donor material.

A "SNP profile" as used herein refers to the allele pattern, i.e., which alleles are present, in a sample.

A "graft" as used herein refers to tissue material, from a donor that is transplanted into a recipient. For example, a graft may be from liver, heart, kidney, or any other organ.

The term "primer" refers to an oligonucleotide that acts as a point of initiation of DNA synthesis under conditions in which synthesis of a primer extension product complementary to a nucleic acid strand is induced, i.e., in the presence of four different nucleoside triphosphates and an agent for polymerization (i.e., DNA polymerase or reverse transcriptase) in an appropriate buffer and at a suitable temperature. A primer is preferably a single-stranded oligodeoxyribonucleotide. The primer includes a "hybridizing region" exactly or substantially complementary to the target sequence, preferably about 15 to about 35 nucleotides in length. A primer oligonucleotide can either consist entirely of the hybridizing region or can contain additional features which allow for the detection, immobilization, or manipulation of the amplified product, but which do not alter the ability of the primer to serve as a starting reagent for DNA synthesis. For example, a nucleic acid sequence tail can be included at the 5' end of the primer that hybridizes to a capture oligonucleotide.

The term "probe" refers to an oligonucleotide that selectively hybridizes to a target nucleic acid under suitable conditions. A probe for detection of the biomarker sequences described herein can be any length, e.g., from 15-500 bp in length. Typically, in probe-based assays, hybridization probes that are less than 50 bp are preferred.

The term "target sequence" or "target region" refers to a region of a nucleic acid that is to be analyzed and comprises the sequence of interest, e.g., a region containing a SNP biomarker.

As used herein, the terms "nucleic acid," "polynucleotide" and "oligonucleotide" refer to primers, probes, and oligomer fragments. The terms are not limited by length and are generic to linear polymers of polydeoxyribonucleotides (containing 2-deoxy-D-ribose), polyribonucleotides (containing D-ribose), and any other N-glycoside of a purine or pyrimidine base, or modified purine or pyrimidine bases. These terms include double- and single-stranded DNA, as well as double- and single-stranded RNA. Oligonucleotides for use in the invention may be used as primers and/or probes.

A nucleic acid, polynucleotide or oligonucleotide can comprise phosphodiester linkages or modified linkages including, but not limited to phosphotriester, phosphoramidate, siloxane, carbonate, carboxymethylester, acetamidate, carbamate, thioether, bridged phosphoramidate, bridged methylene phosphonate, phosphorothioate, methylphosphonate, phosphorodithioate, bridged phosphorothioate or sulfone linkages, and combinations of such linkages.

A nucleic acid, polynucleotide or oligonucleotide can comprise the five biologically occurring bases (adenine, guanine, thymine, cytosine and uracil) and/or bases other than the five biologically occurring bases. These bases may serve a number of purposes, e.g., to stabilize or destabilize hybridization; to promote or inhibit probe degradation; or as attachment points for detectable moieties or quencher moieties. For example, a polynucleotide of the invention can contain one or more modified, non-standard, or derivatized base moieties, including, but not limited to, N6-methyladenine, N6-tert-butyl-benzyl-adenine, imidazole, substituted imidazoles, 5-fluorouracil, 5 bromouracil, 5-chlorouracil, 5-iodouracil, hypoxanthine, xanthine, 4-acetylcytosine, 5 (carboxyhydroxymethyl)uracil, 5 carboxymethylaminomethyl-2-thiouridine, 5 carboxymethylaminomethyluracil, dihydrouracil, beta-D-galactosylqueosine, inosine, N6 isopentenyladenine, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2 thiocytosine, 5-methyl-2-thiouracil, 2-thiouracil, 4-thiouracil, 5-methyluracil, uracil-5-oxyacetic acidmethylester, 3-(3-amino-3-N-2-carboxypropyl) uracil, (acp3)w, 2,6-diaminopurine, and 5-propynyl pyrimidine. Other examples of modified, non-standard, or derivatized base moieties may be found in U.S. Pat. Nos. 6,001,611; 5,955,589; 5,844,106; 5,789,562; 5,750,343; 5,728,525; and 5,679,785, each of which is incorporated herein by reference in its entirety. Furthermore, a nucleic acid, polynucleotide or oligonucleotide can comprise one or more modified sugar moieties including, but not limited to, arabinose, 2-fluoroarabinose, xylulose, and a hexose.

"Repetitive sequences" refer to highly repeated DNA elements present in a genome. These sequences are usually categorized in sequence families and are broadly classified as interspersed repetitive DNA (see, e.g., Jelinek and Schmid, *Ann. Rev. Biochem.* 51:831-844, 1982; Hardman, *Biochem J.* 234:1-11, 1986; and Vogt, *Hum. Genet.* 84:301-306, 1990) or tandemly repeated DNA. Repetitive elements include satellite, minisatellite, and microsatellite DNA. In humans, interspersed repetitive DNA includes Alu sequences, short interspersed nuclear elements (SINES) and long interspersed nuclear elements (LINES), and endogenous retroviruses (ERVs). The categorization of repetitive elements and families of repetitive elements and their reference consensus sequences are defined in public databases (e.g., repbase (version 12.09)—Genetic Information Research Institute (Jurka et al., *Cytogenet Genome Res* 2005; 110:462-7)).

As used herein, the singular forms "a," "an" and "the" include plural referents unless the context clearly dictates otherwise. Thus, for example, reference to "a molecule" includes a plurality of such molecules, and the like.

Introduction

The present invention is based, in part, on the discovery that SNPs having an allele frequency of 0.20 or greater, often 0.30 or greater, and preferably 0.40 or greater, for example, 0.44 or 0.45, or greater, can be surveyed in cfDNA obtained from a transplant patient to identity one or more of such SNP that can be used thereon as a biomarker to monitor rejection status of transplant material. A SNP biomarker identified in accordance with the invention is one for which the transplant recipient is homozygous for the allele and the donor material has an alternative allele. The methods of the invention do not require a separate sample from the donor to identity a SNP biomarker.

Identification of SNPs to Detect Transplant Rejection

A SNP for use in determining a transplantation biomarker in accordance with the invention has a minor allele frequency of at least 0.20 or 0.30 and typically has a minor allele frequency of at least 0.40, 0.41, 0.42, 0.43, 0.44, or 0.45 or greater. Further, such a SNP is not contained within or directly adjacent to a repetitive element. A SNP that is not contained within or directly adjacent to a repetitive element" as used here means that the SNP is sufficiently removed from repetitive sequences such that primers can be designed that specifically amplify the SNP-containing target region. For example, a SNP that is not directly adjacent to a repetitive element may be at a distance of 50 base pairs or greater, upstream or downstream from a repetitive element.

Table 1 provides illustrative SNPs for use in the invention. The SNPs were identified from public databases (e.g, the websites hapmap.ncbi.nlm.nih.gov or www 1000genomes.org). Compilations can also be found for available SNP-arrays, e.g. at the Illumina website for SNPs used on the "HumanOmin5M" SNP chip. As appreciated by one of skill in the art alternative SNPs can be identified based on these criteria.

Allele frequency can vary within different populations. For example, allele frequency may be different in a Caucasian population, such as a Caucasian northern European population in comparison to an Asian population, such as a Japanese population. Accordingly, the determination of a SNP suitable for use for identifying a transplantation SNP biomarker as described herein may also take into account the genetic background information of the transplant recipient and donor with respect to minor allele frequency.

In typical embodiments, a SNP that can be used as a donor biomarker is identified in a sample obtained from the transplant patient without employing a separate sample from a donor. Thus, cfDNA from a patient can be used to identify a SNP biomarker for transplant tissue from a donor. The sample from the patient can be obtained at any given time following transplantation to evaluate donor SNPs.

Detection of Donor Alternative SNP Alleles in Cf DNA

In one embodiment, a blood sample, e.g., serum or plasma sample, from a patient can be evaluated at a later time frame after transplantation, typically at least five days after transplantation, to determine a SNP that can serve as a biomarker for transplantation. At such times, usually less than 10% of graft DNA is present in the cfDNA in a transplant recipient. In this embodiment, a blood sample from the recipient is used to isolate cfDNA. The cfDNA is then subjected to an amplification step to generate a cfDNA library. This initial amplification step to obtain cfDNA library is also referred to herein as a "pre-amplification". Any amplification method can be used to generate the cfDNA library, including, but not limited to PCR. Additional amplification methods are described below. The number of rounds of amplification for this pre-amplification step is sufficient to obtain a quantity of cfDNA library that can be evaluated to identify a SNP from a donor. As an illustrative, non-limiting example, anywhere from 8 to 12 rounds may be performed, although other numbers of rounds may also be performed. The cf DNA is then assessed for pre-selected SNPs that can serve as biomarkers using primers and probes that amplify target regions containing SNPs that were identified as homozygous in the recipient. This analysis is performed using a digital PCR. Those SNPs that provide a signal for a SNP allele that was not identified in the recipient are selected as a transplant biomarker for that transplant patient. Two groups of percentages will be seen: the one that is twice as high as the other e.g., 2% vs 1% is homozygous in the donor transplant material whereas the lower percentage indicates that the SNP is heterozygous in the donor material. The homozygous SNPs are used preferentially for all other samples of the patient. Heterozygous SNPs may also be employed, but are less sensitive.

Any method can be used to determine SNPs that are homozygous in the transplant recipient, including array hybridization, quantitative PCR, sequencing, or an alternative method. In some embodiments, the recipient SNP genotype for SNPs having a minor allele frequency of 0.20 or greater, or 0.30 or greater, or preferably 0.40 or greater, in accordance with the invention, is determined using a pre-amplified cfDNA library as described above. In other embodiments, the SNP profile of the transplant recipient is performed using DNA obtained from peripheral blood leukocytes or other sample from the patient that is free of donor cells. Evaluation of the SNP profile of the recipient using the pre-amplified cfDNA library can employ, but is not limited to, a technique that is not as sensitive as digital PCR to identify recipient SNP alleles. Those SNPs that are homozygous in the patient are used in the analysis of the cfDNA library for donor SNP alleles as described above.

In some embodiments, SNP probes and primers that target one or more SNPs identified in Table 1, e.g., 10, 20, or 30, or more, SNPs identified in Table 1, are used to determine SNPs that are homozygous in the patient. In some embodiments, a SNP probe having a sequence shown in Table 1 is employed.

In some embodiments, the SNP profile for the donor transplant material can be determined using cfDNA isolated from a sample obtained early after transplantation, where much of the cfDNA, e.g., the majority of the cfDNA, is from the graft. In this embodiment, SNP biomarkers are identified using a blood sample obtained from the recipient typically less than one day following transplantation. The cfDNA isolated from the sample is pre-amplified as described above to obtain a cf library. SNPs that are homozygous in the graft are detected by real-time PCR, or an alternative method that does not require digital PCR, although digital PCR may also be employed. Homozygous SNPs are determined in the recipient. For example, DNA is isolated from a recipient sample, e.g., a PBL sample, and used to determine those SNPs that are homozygous. Any method can be used to assess the recipient for homozygous SNP alleles, including real-time PCR, a SNP array and the like. SNPs are then selected where the recipient and the transplant material, i.e., the donor, are each homozygous, but have different alleles for the SNP. These SNPs can be used as biomarkers for future measurements to assess transplant status. In some embodiments, SNP probes and primers that target one or more SNPs identified in Table 1, e.g., 10, 20, or 30, or more SNPs identified in Table 1, are used to determine SNPs that are homozygous in the patient. In some embodiments, a SNP probe having a sequence shown in Table 1 is employed.

As appreciated by one of skill in the art, when cfDNA is used to identify donor SNP alleles to serve as biomarkers, the recipient SNP profile is typically determined first so that only the SNPs that are homozygous in the transplant are surveyed in the cfDNA sample. However, these steps need not be performed in this order. For example, SNPs can be evaluated in the various samples in reactions performed concurrently.

SNPs may also be identified for use as a biomarker where samples from the patient and genetic material from the donor are both available. In this embodiment, DNA isolated from the transplant recipient and donor samples are evaluated for SNPs where the minor allele frequency is 0.20 or higher, typically 0.30 or higher, and preferably 0.40 or higher. In some embodiments, SNP profiles from the patient and donor samples are determined for at least 10, 20, 30, or 40 of the SNPs identified in Table 1. In some embodiments, the SNP evaluation may employ one or more probes having a sequence as shown in Table 1. SNPS where the transplant material and recipient are homozygous, but with different alleles, can then be used for future determination of graft cfDNA percentage.

Amplification of DNA

Amplification reactions are performed on DNA obtained from nucleic acid samples isolated from various recipient or donor sources. For evaluation of samples where it is desired to have only recipient or donor cells present in the sample, peripheral blood leukocytes are conveniently used; however, any other sample from the recipient, or donor, may be employed. Pre-amplification reactions or amplification reactions that do not require the sensitivity of digital PCR can be performed using any number of well-known amplification techniques.

Exemplary references include manuals such as Current Protocols in Molecular Biology, Ausubel, 1994-1999, including supplemental updates through 2013; Sambrook & Russell, *Molecular Cloning, A Laboratory Manual* (3rd Ed, 2001). Although the methods typically employ PCR steps, other amplification protocols may also be used. Suitable amplification methods include ligase chain reaction (see, e.g., Wu & Wallace, *Genomics* 4:560-569, 1988); strand displacement assay (see, e.g., Walker et al., *Proc. Natl. Acad. Sci. USA* 89:392-396, 1992; U.S. Pat. No. 5,455,166); and several transcription-based amplification systems, including the methods described in U.S. Pat. Nos. 5,437,990; 5,409,818; and 5,399,491; the transcription amplification system (TAS) (Kwoh et al., *Proc. Natl. Acad. Sci. USA* 86:1173-1177, 1989); and self-sustained sequence replication (3SR) (Guatelli et al., *Proc. Natl. Acad. Sci. USA* 87:1874-1878, 1990; WO 92/08800). Alternatively, methods that amplify the probe to detectable levels can be used, such as Qβ-replicase amplification (Kramer & Lizardi, *Nature* 339:401-402, 1989; Lomeli et al., *Clin. Chem.* 35:1826-1831, 1989). In some embodiments, DNA is amplified using adaptor-ligation and single primer PCR. Other available methods of amplification, such as balanced PCR (Makrigiorgos, et al., *Nature Biotechnol,* 20:936-9 (2002)) and isothermal amplification methods such as nucleic acid sequence based amplification (NASBA) and self-sustained sequence replication (Guatelli et al., *PNAS USA* 87:1874 (1990)). In some embodiments, multiplex reactions can be performed in which multiple target regions are amplified and detected in a single reaction.

Digital PCR

Digital PCR is a technique where a limiting dilution of the sample is made across a large number of separate PCR reactions so that most of the reactions have no template molecules and give a negative amplification result. Those reactions that are positive at the reaction endpoint are counted as individual template molecules present in the original sample in a 1 to 1 relationship. (See, e.g., Kalina et al. NAR 25:1999-2004 (1997) and Vogelstein and Kinzler, PNAS 96:9236-9241 (1999); U.S. Pat. Nos. 6,440,706, 6,753,147, and 7,824,889.) Quantitative partitioning is assumed, and the dynamic range is governed by the number of containers available for stochastic separation. The molecules are then detected by PCR and the number of positive containers is counted. Each successful amplification is counted as one molecule, independent of the actual amount of product. In some embodiments, a digital PCR may be a microfluidics-based digital PCR. In some embodiments, a droplet digital PCR may be employed.

One of skill in the art can readily design primers and probes to target regions of a SNP of interest. As described above, a SNP that is evaluated as a potential transplant biomarker in accordance with the invention has a minor allele frequency of at least 0.20 or at least 0.30, and preferably at least 0.40, 0.41, 0.42, 0.43, 0.44, or 0.45, or greater. Such primers and probes are used to detect individual SNP alleles.

In some embodiments, SNP-specific amplification methods can be used (e.g., using SNP-specific amplification primers). In some embodiments, primers are used to amplify a target region and the SNP alleles are detected using probes specific for each allele. Oligonucleotides that are employed as primers and/or probes to detect biomarkers can be selected using methods well-known in the art. For example, PCR primers may be designed using standard primer design computer software techniques known to individuals skilled in the art. The variables considered during PCR primer design may include primer length, GC pair content, melting temperature, and size of the target nucleic acid amplified by the primer pair.

In one embodiment, the biomarker is identified by hybridization under sequence-specific hybridization conditions with a probe that targets the biomarker region (e.g., targets some unambiguously assigned portion of, the target biomarker) with or without a preceding amplification of DNA. Principals for designing such a probe are well known in the art.

Use of Transplant Biomarkers

A SNP transplant biomarker identified in accordance with the invention may be used to evaluate transplant rejection status in the recipient. Such an evaluation can be performed, e.g., using an amplification reaction to detect transplant biomarker in the cfDNA present in a blood sample from the patient. The cfDNA of the patient may be evaluated periodically, for example, over the course of days, weeks, months, or years, for SNP biomarkers in cfDNA to monitor the status of the transplant, i.e., whether there are signs of rejection or damage. If the percentage of graft cfDNA rises either higher than the mean, typically +2SD of values seen in uncomplicated courses, or shows a sustained increase, this is indicative of a rejection.

In order to detect the presence of the transplant biomarker, a blood sample is obtained from the patient at the desired time point following transplant. A cfDNA sample is obtained from the blood sample and is analyzed to determine the level of donor material by identifying the presence of donor SNP alleles in the cfDNA. Any method can be used to evaluate the sample. In typical embodiments, digital PCR, such as a microfluidics-based digital PCR or droplet-based PCR is employed. Other methods can be based on direct hybridization of detection probes (without prior amplification) or sequencing, e.g., sequencing of an amplicon defined in Table 1. For example, the SNP region is amplified by PCR and then the percentage of the minor allele is determined by amplicon sequencing. The percentage of donor cfDNA (also referred to as graft cfDNA) in the cfDNA sample can be determined. In other embodiments, the copy number of donor cfDNA is determined.

Analysis of graft cfDNA levels in the blood using a SNP analysis as described herein can be used to detect any kind of injury to or deterioration of transplant organ cells. For example, graft cfDNA analysis can be used to assess perfusion injury. Typically, monitoring graft cfDNA to determine the presence of reperfusion injury comprises monitoring cfDNA samples from the transplant recipient that are obtained soon after transplant, e.g., within 7 days of transplant. In the context of the present invention, the term "perfusion" is used interchangeably with "reperfusion".

In some embodiments, damage that arises from reactivation of a virus infection, e.g., a hepatitis virus infection, can be assessed using a SNP graft cfDNA assay in accordance with the invention. In some embodiments, such methods further comprise identifying the presence of the virus, e.g., where the transplant is a liver, the presence of a hepatitis virus.

In some embodiments, evaluation of graft cfDNA in a transplant recipient using the methods described herein is employed to monitor the status of a donor organ that is a marginal organ. A "marginal organ" is an art-recognized term that describes an organ from a donor that has a medical history that does not meet the optimal history for organ donors, for example, the donor, may have one of the following criteria: extremes of age, adverse past medical history, etc. These criteria vary from organ to organ and depend on the patient history.

In some embodiments, graft cfDNA SNP analysis in accordance with the invention can be used to adjust an immunosuppressive regimen in a patient. For example, the lowest effective amount of an immunosuppressive drug regimen that achieves a level of graft cfDNA that is observed in stable transplant patients can be determined. Typically, monitoring the status of the graft to adjust an immunosuppressive regimen comprises monitoring cfDNA samples from the transplant recipient that are obtained at about ten days or two weeks or longer. Monitoring can be performed for an extended period of time of up to years at desired intervals.

In some embodiments, graft cfDNA analysis in accordance with the invention can be used to detect a solid organ transplant injury caused by donor-specific antibodies. A transplant recipient can be monitored over the course of years for such damage. In some embodiments, a method of the invention may further comprise detecting the presence of donor-specific antibodies circulating in the blood of the transplant recipient. Such antibodies are specific for the HLA type of the donor organ and can be detected using known assays. In some embodiments, a patient having such donor-specific antibodies may be additionally treated with immunosuppressive agents that suppress B cells.

The information obtained from the SNP biomarker analysis may be stored in a computer readable form. Such a computer system typically comprises major subsystems such as a central processor, a system memory (typically RAM), an input/output (I/O) controller, an external device such as a display screen via a display adapter, serial ports, a keyboard, a fixed disk drive via a storage interface and a floppy disk drive operative to receive a floppy disc, and a CD-ROM (or DVD-ROM) device operative to receive a CD-ROM. Many other devices can be connected, such as a network interface connected via a serial port.

The computer system may also be linked to a network, comprising a plurality of computing devices linked via a data link, such as an Ethernet cable (coax or 10BaseT), telephone line, ISDN line, wireless network, optical fiber, or other suitable signal transmission medium, whereby at least one network device (e.g., computer, disk array, etc.) comprises a pattern of magnetic domains (e.g., magnetic disk) and/or charge domains (e.g., an array of DRAM cells) composing a bit pattern encoding data acquired from an assay of the invention.

The computer system can comprise code for interpreting the results of a study to determine SNP transplant biomarkers or to evaluating the presence of one or more of the SNP transplant biomarkers identified in accordance with the invention to aid in prognosis. Thus in an exemplary embodiment, the biomarker analysis results are provided to a computer where a central processor executes a computer program for evaluating the one or more biomarkers.

The invention also provides the use of a computer system, such as that described above, which comprises: (1) a computer; (2) a stored bit pattern encoding the biomarker testing results obtained by the methods of the invention, which may be stored in the computer; (3) and, optionally, (4) a program for evaluating a biomarker.

The invention further provides methods of generating a report based on the detection of one or SNP transplant biomarkers for the patient.

Thus, the present invention provides systems related to the above methods of the invention. In one embodiment the invention provides a system for analyzing circulating cell-free DNA, comprising: (1) a sample analyzer for executing the method of analyzing circulating cell-free DNA in a patient's blood, serum or plasma as described in the various embodiments above; (2) a computer system for automatically receiving and analyzing data obtained in step (1) to provide a test value representing the status (presence or absence or amount, i.e., concentration or copy number) of a SNP transplant biomarker for the patient.

The computer-based analysis function can be implemented in any suitable language and/or browsers. For example, it may be implemented with C language and preferably using object-oriented high-level programming languages such as Visual Basic, SmallTalk, C++, and the like. The application can be written to suit environments such as the Microsoft Windows™ environment including Windows™ 8, Windows™ 7, Windows™ 98, Windows™ 2000, Windows™ NT, and the like. In addition, the application can also be written for the MacIntosh™, SUN™, UNIX or LINUX environment. In addition, the functional steps can also be implemented using a universal or platform-independent programming language. Examples of such multi-platform programming languages include, but are not limited to, hypertext markup language (HTML), JAVA™, JavaScript™, Flash programming language, common gateway interface/structured query language (CGI/SQL), practical extraction report language (PERL), AppleScript™ and other system script languages, programming language/structured query language (PL/SQL), and the like. Java™- or JavaScript™-enabled browsers such as HotJava™ or Microsoft™ Explorer™ can be used. When active content web pages are used, they may include Java™ applets or ActiveX™ controls or other active content technologies.

The analysis function can also be embodied in computer program products and used in the systems described above or other computer- or internet-based systems. Accordingly, another aspect of the present invention relates to a computer program product comprising a computer-usable medium having computer-readable program codes or instructions embodied thereon for enabling a processor to carry out the analysis and correlating functions as described above. These computer program instructions may be loaded onto a computer or other programmable apparatus to produce a machine, such that the instructions which execute on the computer or other programmable apparatus create means for implementing the functions or steps described above. These computer program instructions may also be stored in a computer-readable memory or medium that can direct a computer or other programmable apparatus to function in a particular manner, such that the instructions stored in the computer-readable memory or medium produce an article of manufacture including instruction means which implement the analysis. The computer program instructions may also be loaded onto a computer or other programmable apparatus to cause a series of operational steps to be performed on the computer or other programmable apparatus to produce a computer implemented process such that the instructions which execute on the computer or other programmable apparatus provide steps for implementing the functions or steps described above.

The following examples are provided by way of illustration only and not by way of limitation. Those of skill in the art will readily recognize a variety of non-critical parameters that could be changed or modified to yield essentially similar results.

EXAMPLES

Example 1. Quantification of Donor Cell-Free DNA

Methods
SNP Assays

SNPs were selected from public databases considering those which show a known and validated minor allelic frequency of >40% in Caucasians and >45% over all reported ethnicities. As a next step, SNP that are in or directly adjacent to a repetitive element were eliminated. The remaining SNPs were then investigated for their usefulness in a probe hydrolysis assay. This was done in silico by using thermodynamic calculations (Schütz & von Ahsen, *Biotechniques* 27:1218-1222, 1224, 1999) to optimize the binding differences for the two probes that hybridize to the two alleles at the desired temperature of 65° C. at standard PCR buffer conditions (e.g. 0.18 mol/L salt and 0.5 µmol/L DNA/primer). Because the slope of a dsDNA probe melting curve is mainly dependent on the enthalpy of the probes (Marky & Breslauer, *Biopolymers* 26:1601-1620, 1987), the latter dominates the selection for a maximized difference of free Gibbs energy between allele binding at a given condition. A total of 41 probe sets (Table 1) were designed with one probe for each of the two alleles where FAM and HEX were used in conjunction with BHQ1 as quencher. Respective PCR primers were designed to exhibit a Tm of 68° C. and a binding of >95% at 60° C.

Each of the assays was first optimized in a LightCycler480, using the ddPCR Supermix for Probes (Bio-Rad) and subsequently optimized for digital droplet PCR (ddPCR), which yielded slightly different cycling conditions. Two different annealing temperatures were established in order to maximize efficiency and differentiation of alleles.

Table 1 lists probes and other characteristics for each of the selected SNPs. Table 1 part A: Col. 1, SNP designation in Table 1; Col. 2, SNP name/reference; Col. 3, chromosome; Col 4, position on chromosome; Col. 5, minor allele frequency (MAF) (all populations); Col. 5, MAF, Caucasian; Cols. 6 and 7: illustrative primers for amplification of target region containing SNP; Col. 8, Annealing and Extension temperatures. Table 1 part B: Col. 1, SNP designation in Table 1; Col. 2, SNP (nucleotide change); Col. 3, length of amplicon containing SNP obtained with primers shown in part A, Cols. 6 and 7; Cols. 4-7, SNP probes and characteristics.

TABLE 1

| part A | | | | | | | | |
|---|---|---|---|---|---|---|---|---|
| Short Name | Name | Chr | Pos (Mb) | MAF (all) | MAF (Caucasian) | Forward primer (SEQ ID NO:) | Reverse Primer (SEQ ID NO:) | Annealing & Extension °C. |
| S43 | GA002729 | 2 | 217.6 | 47.1% | 47.1% | Gtctctggggtctgttggcc (1) | Agaggaaggactcccaggggg (2) | 61 |
| S46 | kgp2846187 | 16 | 13.3 | 49.1% | 49.1% | Tccagcagaggaaatagtacttgc (3) | Agccacctggtctccttca (4) | 59 |
| S38 | kgp3586059 | 10 | 71.6 | 48.6% | 48.6% | Tcaatcctcacaacttccctaaggg (5) | Agtgggagggaggtacagtga (6) | 61 |

TABLE 1-continued part A

| Short Name | Name | Chr | Pos (Mb) | MAF (all) | MAF (Caucasian) | Forward primer (SEQ ID NO:) | Reverse Primer (SEQ ID NO:) | Annealing & Extension °C. |
|---|---|---|---|---|---|---|---|---|
| S48 | kgp3469073 | 16 | 87.7 | 48.8% | 48.8% | Ggggtgtggggtgaggga (7) | Gcgcggctggggtgttta (8) | 61 |
| S50 | kgp5728993 | 1 | 4.8 | 48.5% | 48.5% | Tcttgtcgaggctgccctgaaagg (9) | Acagagccggccggtcgc (10) | 61 |
| S51 | kgp7257211 | 15 | 96.7 | 48.8% | 48.8% | Ctgacccaattgtgtgtcagagca (11) | Tcttgagcaccttaccagccttcaca (12) | 61 |
| S53 | kgp779610 | 8 | 104.2 | 48.7% | 48.7% | Tgtgggcagtctcactgagga (13) | Accccccagtgtggctctgct (14) | 59 |
| S54 | kgp8186648 | 7 | 7.8 | 49.4% | 49.4% | Acctgccccctagaaaactgct (15) | Gcagtactatactagaaacacatggcagc (16) | 59 |
| S55 | kgp9738136 | 18 | 3.8 | 49.7% | 49.7% | Cgccccaaattgcgcacaacca (17) | Acttccctcccaaccccaccact (18) | 61 |
| S57 | rs2523860 | 6 | 31 | 49.9% | 49.9% | Cagcctctggttccaggcct (19) | Ggagaatcccagaagcaggctga (20) | 59 |
| S58 | kgp10934323 | 2 | 47.9 | 49.9% | 49.9% | Gtgcagcccctgttcatgcct (21) | Catgccaggccaggggtgg (22) | 59 |
| S59 | kgp12078903 | 8 | 20.8 | 48.7% | 48.7% | Agaaagaaagaagcagggaagggac (23) | Tggagctaaaatgagcctgcgt (24) | 61 |
| S63 | kgp5942754 | 7 | 153.1 | 49.3% | 49.3% | Gctgttgctgcctcacaggt (25) | Agggcaaaggcaaatgcacca (26) | 61 |
| S66 | kgp7251638 | 11 | 80.8 | 50.0% | 50.0% | Accctgaccctcagttcctt (27) | Aagagccctataaggtgtgagaaa (28) | 61 |
| S67 | kgp7882745 | 19 | 30.1 | 43.5% | 43.5% | Atgaagagtaagcggggccg (29) | Cggacccatttcacccacca (30) | 61 |
| S68 | kgp88374 | 8 | 105.4 | 46.7% | 46.7% | Ggacactcactggggcctct (31) | Aggactgaaactagaagaaaaggtcgg (32) | 59 |
| S70 | rs6436409 | 2 | 224.4 | 49.1% | 49.1% | Tggcccagttagaaggtgtgga (33) | Cggccacccatcctggagat (34) | 61 |
| S77 | rs2072042 | 16 | 1 | 49.7% | 49.7% | Gggcctcagttctagacgagt (35) | Gtttccgtgaagtaggcgct (36) | 61 |
| S78 | kgp12502655 | 7 | 55 | 49.1% | 49.1% | Aggcagaactaaacgttggctt (37) | Tgcggaacagtgacaatttgttc (38) | 59 |
| S79 | rs11103106 | 9 | 138.5 | 49.7% | 49.7% | Cagggagtgctttactgaggca (39) | Actcaaacacggagctgggc (40) | 59 |
| S80 | kgp3747074 | 6 | 3.5.7 | 50.0% | 50.0% | Aacttagctgctcttgcttcagt (41) | Gtacctgcctaactcagtatgatctt (42) | 61 |
| S82 | rs10228737 | 7 | 4.2 | 49.7% | 49.7% | Ttttgcacttgacgcaccagc (43) | Ccgaggcagaggaaggaagtg (44) | 61 |
| S83 | rs13317873 | 3 | 150.9 | 49.7% | 49.7% | Ggttttcgttctgatgatccctct (45) | Agcattgtgtagggactggtaaatt (46) | 61 |
| S84 | rs10164176 | 18 | 44.8 | 49.3% | 49.3% | Ccccaaactaagtacctaatcactcgt (47) | Ccaaggggacgatccaccat (48) | 61 |
| S85 | rs251022 | 5 | 140.9 | 49.9% | 49.9% | Acacacacacacgcaattcgg (49) | Atgagctgaggtgggtgctg (50) | 61 |
| S86 | rs12096438 | 1 | 25.9 | 50.0% | 50.0% | Gtctccctcccaaaggtgc (51) | Gccaacctcaagggggcagtt (52) | 59 |
| S87 | rs10734083 | 10 | 131 | 49.9% | 49.9% | Ggcatctgaattcaagctttggtc (53) | Ttcttctagtttggtctggtaggct (54) | 61 |
| S88 | kgp187715 | 19 | 41.1 | 49.7% | 49.7% | Tggttattgttactaggctcccccacc (55) | Agaataagcaagatgttggcagtgag (56) | 61 |
| S90 | kgp5357482 | 22 | 25.5 | 49.6% | 49.6% | Tggttgaacgtccacagaagga (57) | Caagcacacgtggctgctc (58) | 59 |
| S91 | rs2298065 | X | 44 | 49.6% | 49.6% | Gcagagggaagaagaaggca (59) | Gcagtagataactctggctttcagc (60) | 59 |
| S92 | kgp5971873 | 5 | 149.6 | 48.8% | 48.8% | Gtgagcagaatccaagcttcagc (61) | Ccccacctcataacaaccctc (62) | 61 |
| S94 | rs7072759 | 10 | 18.6 | 49.1% | 49.1% | Ctggggcagagtggagagtc (63) | Atccacctctgaacccagcc (64) | 61 |
| S96 | kgp5873854 | 15 | 70.7 | 49.7% | 49.7% | Tcccaggctcaggtcagat (65) | Ggatcaatgtggctgctccct (66) | 61 |
| S97 | kgp9771053 | 18 | 8.6 | 49.6% | 49.6% | Agccctgcacactcacttacc (67) | Tggcattcagatcatcaggcttct (68) | 59 |
| S99 | rs12064796 | 1 | 20.1 | 49.6% | 49.6% | Ggcaaagtgggcaagggtct (69) | Gcctcctaaagcttgagccaca (70) | 61 |
| S102 | kgp1474040 | 13 | 27.6 | 49.4% | 49.4% | Aacagtggcagccctcttgt (71) | Acacttggttcatgggttctgtg (72) | 59 |
| S103 | rs4632826 | 5 | 141.9 | 49.3% | 49.3% | Agctttcttgcttctgcccca (73) | Gggtgccattgcccagagat (74) | 61 |
| S105 | rs1265094 | 6 | 31.1 | 49.1% | 49.1% | Accccaagaggctttataggg (75) | Ccttcccaacggggtttgacc (76) | 61 |
| S107 | kgp4246032 | 9 | 28 | 49.9% | 49.9% | Cttccttgccctcttcca (77) | Gctctgtggatccctggag (78) | 59 |
| S108 | rs11610836 | 12 | 113.2 | 49.0% | 49.0% | Acactctgctgcgtgtctg (79) | Ttcctcccaccactcccat (80) | 61 |
| S110 | rs13185616 | 5 | 13.7 | 49.7% | 49.7% | Ggtcctaccgaggtgggtga (81) | Cattgccaaggacagagggaga (82) | 61 |

TABLE 1-B

| Short Name | SNP | Length of Amplicon (bp) | Probe_A* (SEQ ID NO:) | Probe_B* (SEQ ID NO:) | ΔG-Matching Allele** | | ΔG-Non-Matching Allele** | |
|---|---|---|---|---|---|---|---|---|
| | | | | | ProbeA | ProbeB | ProbeA | ProbeB |
| S43 | C > G | 100 | tggagacgggtccgCagag (83) | tggcacaggtgctctCcgg (84) | −1.19 | −1.57 | 2.33 | 1.54 |
| S46 | C > G | 90 | ctggggagagaaagaacaaaCagcat (85) | catttccccaaatgctCtttgttct (86) | −0.08 | −0.19 | 3.61 | 3.25 |
| S38 | C > G | 90 | aaaaggggtggtgtCaatgtc (87) | agggactgacattCacaccacc (88) | −0.04 | −0.80 | 2.59 | 1.83 |
| S48 | C > G | 91 | cgggagccctgcgCtttg (89) | tttccatgacaaaCcgcaggg (90) | −1.59 | −0.09 | 2.74 | 4.08 |
| S50 | C > G | 91 | cggttttcgctcCcgtgaa (91) | agtccatttcacgCgagcg (92) | −0.32 | −0.30 | 3.74 | 4.18 |
| S51 | C > G | 106 | ctttagctgccaagaaggatCagag (93) | agaatgtgtgttctcactctCatcct (94) | −0.63 | −0.66 | 2.00 | 1.96 |
| S53 | C > G | 107 | aggCctgggtggagaagt (95) | ccagCccttgtctcaaaagcc (96) | −0.42 | −0.13 | 3.58 | 3.87 |
| S54 | C > G | 171 | atgaaaccaagcagtaCtgtggaat (97) | accaacaaattccacaCtactgct (98) | −0.13 | −0.17 | 4.38 | 4.33 |
| S55 | C > G | 98 | acttctcagcaacagCctgga (99) | ctctggaaattcatccagCctgt (100) | −0.52 | −0.44 | 3.48 | 3.56 |
| S57 | C > G | 107 | cactcacgtttgggatacttCgtttc (101) | cccagtaaggaatggagaaacCaagta (102) | −0.14 | −0.26 | 3.45 | 3.32 |
| S58 | C > G | 87 | attacaggcatgagCcaccg (103) | caaggcacgtgCctcat (104) | −0.40 | −0.06 | 3.60 | 3.94 |
| S59 | C > G | 92 | attacatagcttatcaCttgcagagcc (105) | actcctggctctgcaaCtgat (106) | −0.08 | −0.24 | 4.42 | 4.26 |
| S63 | C > G | 103 | aactggaagtaacacCtgcacca (107) | cttgactcttggtgcaCtgtgt (108) | −0.42 | −0.17 | 3.97 | 4.48 |
| S66 | C > G | 98 | aggatattgctagagtggagtCagaac (109) | accactgttatttgttctCactccact (110) | −0.13 | −0.82 | 2.50 | 1.81 |
| S67 | C > G | 86 | cccgaccccttaacCtcccc (111) | tggagagggttggggaCgtta (112) | −0.12 | −0.39 | 4.27 | 4.26 |
| S68 | C > G | 105 | agacaCttgtgggactcagaagg (113) | acaaCtgtctcctgctgtcct (114) | −0.49 | −0.43 | 4.01 | 4.07 |
| S70 | C > G | 97 | accctcctgtactgCgcacc (115) | acagtgaaggtgtgcCcagt (116) | −0.66 | −0.60 | 3.82 | 3.47 |
| S77 | T > C | 96 | atgctcagcacacAgggga (117) | cactgcttccccCgtgtg (118) | −0.18 | −0.03 | 2.80 | 4.10 |
| S78 | A > G | 88 | atgcAgctttggcatgaggt (119) | atgccaaagcCgcatattttctct (120) | −0.29 | −0.54 | 2.68 | 3.58 |
| S79 | A > G | 98 | ggcagcaggtgccAagca (121) | aggcattactgctCggcacc (122) | 0.17 | 1.12 | 2.47 | 2.40 |
| S80 | A > G | 96 | cccagcaggaaagcgAgtc (123) | aagtaagaatcagacCcgcatttcc (124) | −0.53 | −0.04 | 2.06 | 3.70 |
| S82 | T > C | 79 | tgcAatgagagcagaggcct (125) | catCgcagccctcctgca (126) | −0.04 | −0.19 | 2.60 | 3.33 |
| S83 | T > C | 116 | atacActctgttgtgagtgccac (127) | cagagCgtgtatgtaagtccagagt (128) | −0.02 | −0.16 | 2.86 | 4.02 |
| S84 | T > C | 96 | cccaCggggaggaatgtctttg (129) | cccAtggacttctggcc (130) | −0.69 | −0.25 | 2.55 | 1.89 |
| S85 | A > G | 94 | acacaAagtggcctcccg (131) | acaGagtggcctcccgat (132) | −0.15 | −0.24 | 2.15 | 2.34 |

TABLE 1-B-continued

| Short Name | SNP | Length of Amplicon (bp) | Probe_A* (SEQ ID NO:) | Probe_B* (SEQ ID NO:) | ΔG-Matching Allele** ProbeA | ΔG-Matching Allele** ProbeB | ΔG-Non-Matching Allele** ProbeA | ΔG-Non-Matching Allele** ProbeB |
|---|---|---|---|---|---|---|---|---|
| S86 | T > C | 95 | aggaaagaaaccttttcAgatgtcagt (133) | tgaggattaactgacatcCgaaaggt (134) | −0.06 | −0.31 | 2.92 | 3.81 |
| S87 | T > C | 94 | aggcttgtacactCtccccc (135) | acactgggatgggggaAagt (136) | −0.35 | −0.61 | 2.56 | 1.69 |
| S88 | C > G | 95 | aggacatattggggaggCtgac (137) | ctggaagccaaagtcaCcctc (138) | 0.76 | 0.36 | 3.56 | 3.82 |
| S90 | A > C | 89 | cagTgccctctgccaggaa (139) | gggcCctgcctgagcatag (140) | −0.49 | −0.51 | 2.51 | 3.39 |
| S91 | A > C | 96 | cctcctcacccaaaattttagt (141) | tggggTgaggaggactgga (142) | −0.28 | −0.03 | 3.62 | 2.98 |
| S92 | A > G | 149 | ccCgcagttgcacagcttg (143) | actgcAggccacaaggtg (144) | −0.71 | −0.09 | 3.42 | 2.89 |
| S94 | A > G | 83 | aggacActgcagctgtgg (145) | cagCgtcctctgtgctacct (146) | −0.06 | −0.50 | 2.82 | 3.69 |
| S96 | T > C | 81 | tctccgcccttctgagatgc (147) | agggcAgagactctggact (148) | −0.13 | −0.19 | 3.99 | 2.79 |
| S97 | A > G | 83 | ccatcaggtgctggcActc (149) | tgcaggga agagCgccag (150) | −0.55 | −0.28 | 2.33 | 3.91 |
| S99 | A > G | 96 | ttggggccaGgtacctgg (151) | tggggccaAgtacctggt (152) | −0.31 | −0.02 | 2.26 | 2.62 |
| S102 | C > G | 80 | tggccttatctttggccctaaCatg (153) | aggcacatcctacatCttagggc (154) | −0.97 | −0.58 | 2.72 | 2.85 |
| S103 | T > C | 143 | ccctggggccatcaGgtt (155) | ccctggggccatcaAgttt (156) | −1.22 | −0.52 | 1.35 | 2.12 |
| S105 | A > G | 96 | ccactgggctggCccctc (157) | agtggaggaggAccagc (158) | −1.66 | −0.26 | 2.14 | 2.24 |
| S107 | T > C | 76 | aggttgtgtgaaAgtgccct (159) | agccctcagggcacCttca (160) | −0.12 | −0.32 | 2.52 | 3.20 |
| S108 | T > C | 96 | ggtcccagctggtCgtgg (161) | atgctccccacAaccagct (162) | −0.70 | −0.81 | 2.81 | 1.83 |
| S110 | A > C | 90 | tttggtagggaaggaactcCcaat (163) | atcagtggccattgTgagacc (164) | 0.15 | 0.25 | 3.75 | 2.76 |

Samples

For initial assay establishment and optimization, genomic DNA and cfDNA were extracted from EDTA-anticoagulated blood collected from healthy volunteers. Within one hour after collection, plasma was separated from the cells by centrifugation (2500×g for 10 min at 4° C., followed by a second centrifugation of the plasma at 4000×g for 20 min at 4° C. to remove any cell debris. DNA from both the plasma (>1 mL) and the harvested buffy coat was extracted with the Roche Total Viral Acid Extraction Kit using manufacturer's instructions. The results reported here were from samples that were drawn under an IRB approved protocol with informed consent.

Samples were either from patients early (<4 months) after transplantation (Liver: LTx, n=6) or from stable outpatients during the later maintenance course after transplantation of liver (LTx, n=9), heart (HTx, n=8), and Kidney (KTx, n=9).

Library Construction

Typically, about 1,000 to 1,500 genome copies are expected to be present in one mL of blood. The recovery if 2 mL EDTA plasma is used, therefore, is about 4,000 to 6,000 copies. If 2% are to be detected in a quantitative manner, the required number of fragments for testing of several SNPs can only be achieved if a pre-amplification is performed. For this purpose, we used the NEBNext Ultra DNA Library Prep Kit (New England Biolabs), since this gave the best efficiency at amounts as low as 5 ng of DNA, which reflects the usual amount of cfDNA, when samples as given above. We amplified the ligated cfDNA to 1,100 ng on average (SD: 325) using a maximum of 11 PCR cycles using real-time monitoring of library amplification in a LightCycler480 (Roche Applied Sciences).

Digital Droplet PCR ddPCR reactions were prepared using the ddPCR Supermix for Probes (Bio-Rad). Each reaction contained 30 ng or 100 ng of the cfDNA library as template, 900 nmol/L of each primer and 250 nmol/L of each probe. Droplets were generated using the QX100 droplet generator (Bio-Rad) according to the manufacturer's protocols. The cycling conditions were: 95° for 10 min, 50×(94° for 30 sec, 95°/61° for 1 min), 98° for 10 min. Droplets were read in the QX100 droplet reader and analyzed using the software Quantasoft version 1.3.2.0 (Bio-Rad). For the quantification of the minor allele fractional abundance, the embedded "Rare Event Detection" calculation was used, which basically takes the underlying Poisson distribution into account to calculate the template molecule concentration of either allele. These values are then used to express the minor allele in percent of the total concentration.

Results

Analytics

We first investigated how sensitive the methods were in terms of the limits of detection of minor amounts of one allele. To do so, known amounts of genomic DNAs with known genotypes per SNP were mixed at a minor allele concentration of 2%. The intra-assay precision was determined in series of 9 repetitions in one run to calculate a coefficient of variation (CV). FIG. 1 illustrates CV profiles for 13 of the SNP assays. It can be seen that even at a 2% minor allele content a CV of <15% (range 4%-14%) was achieved, which is comparable to the theoretical obtainable CV as based on the number of droplets positive for the minor allele (151 SD:54). The reported CVs were sufficient for the purpose of graft DNA detection. The recovery of the spiked in 2% was on average 1.87% (94% of spiked value) over the thirteen SNP assays with a standard deviation of 0.24% (13%).

Figure 2:
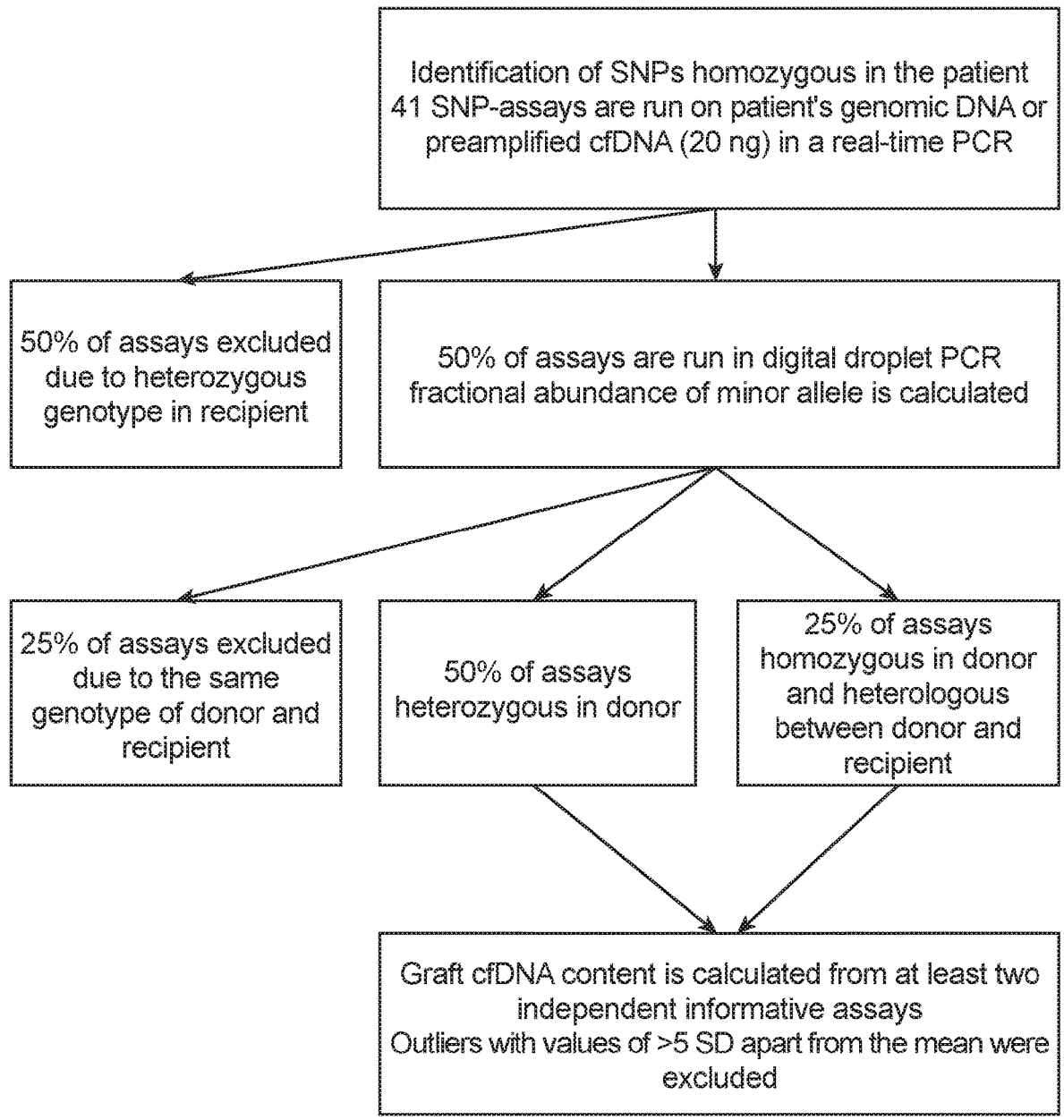
FIG. 2 provides a schematic of the workflow deployed to obtain measures of graft cfDNA content.

FIG. 2 illustrates a procedure deployed to determine the graft DNA content in the recipients' circulation. In order to select those SNPs for each recipient that gives the highest theoretical sensitivity, one sample was tested for all SNPs on one LightCycler480 run. SNPs heterozygous in the recipient were eliminated from the consecutive ddPCRs. If multiple samples from one patient were to be tested, only one sample was used for this pre selection step. This yielded on average 17 (SD: 4) useful SNP assays for each of the tested recipients (n=32).

Figure 3:
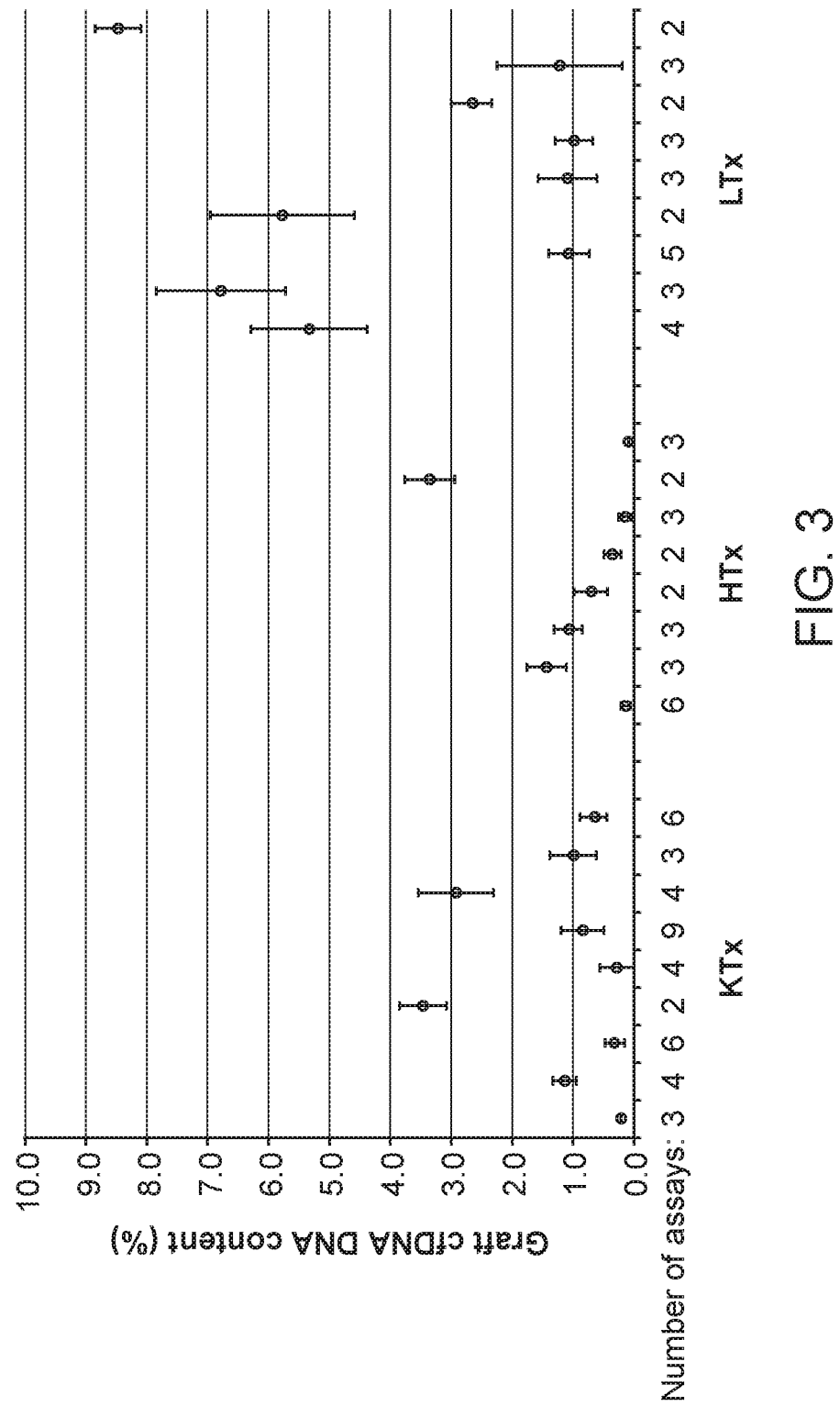
FIG. 3 provides illustrative data for the graft cfDNA content measured in the circulation of 10 stable LTx, 9 stable KTx and of 8 stable HTx patients.

The ddPCRs of the clinical samples were performed using 30 ng (LTx samples) or 100 ng (HTx and KTx samples) of the cfDNA library per well, which translated to about 0.5 and 1.5 copies per droplet respectively. FIG. 3 show the results for stable liver, kidney and heart transplant recipients with no signs of rejection. A total of 10 different ddPCR assays were performed for the LTx patients, and a total of 16 different ddPCR assays were performed for the KTx and HTx patients. The number of informative assays used to determine the graft cfDNA content is given below the abscissa. The percentage of graft DNA in the circulation of liver recipients was lower than 10% in all patients. The average amount of graft DNA was 3.7% (SD: 2.9%) in the LTx group (n=10). The KTx (n=9) and HTx (n=8) average graft DNA contents with 1.2% (SD: 1.2%) and 0.9% (SD:

1.1%) are lower. The higher amount in LTx compared to the other organs may reflect the higher regeneration rate that is usually seen for hepatocytes compared to other e.g. heart and kidney cells.

Figure 4:
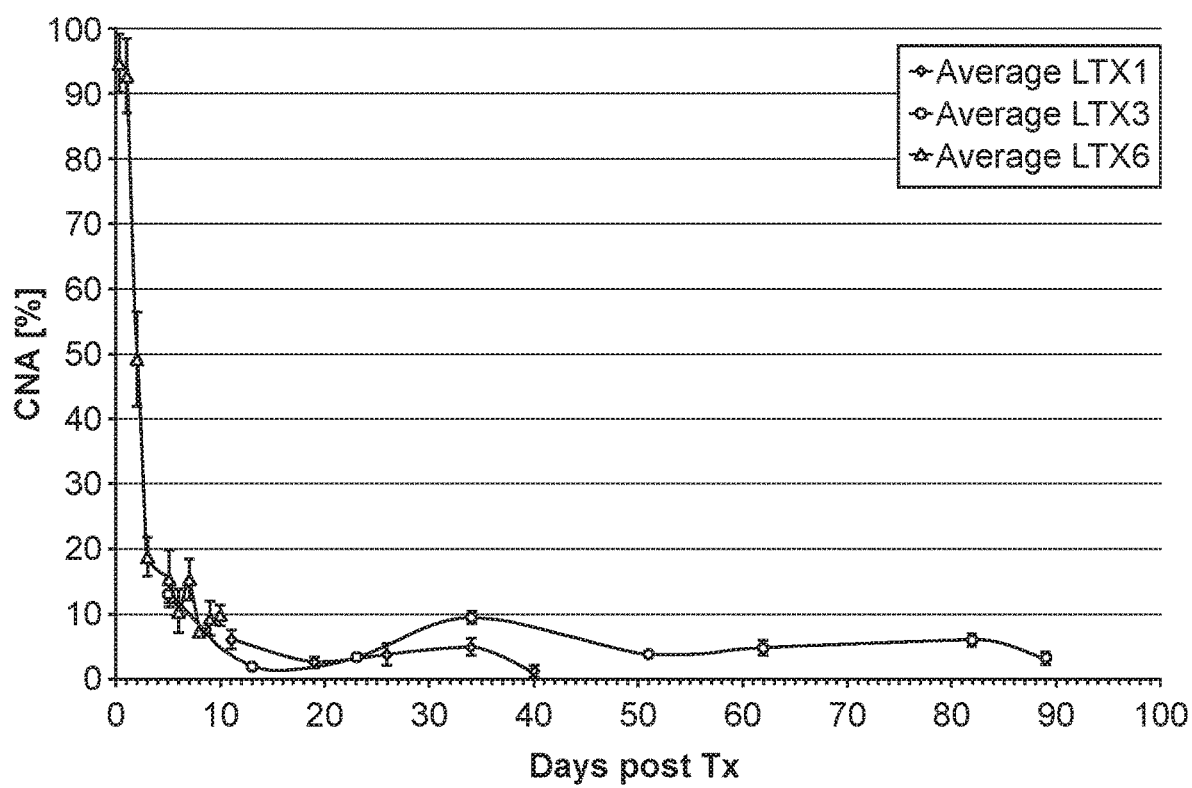
FIG. 4 provides illustrative data of a timecourse measurement of cfDNA content in the circulation of 3 patients with liver transplantations. The earliest sample analyzed was obtained from patient LTx6 at day 1 after surgery. Nearly 100% of the cfDNA in the patient's plasma is graft derived DNA.

In the early (acute) phase after LTx the detected amount of graft cfDNA was very different from the stable phase, most probably reflecting the ischemia/reperfusion damage and the recovery from that. We analyzed samples within 5 hrs after re-establishing blood flow to the donated organ. FIG. 4 shows the time course of the graft cfDNA in this patient, who later had excellent recovery of graft function. During the early post-engraftment phase graft DNA was the vast majority of the cfDNA (up to >95%), but then decreased with an approximate half-life of 24 hours. Five patients were followed early after LTx. Of these, 3 had no severe reported complications or rejection episodes during the first 3 months. The total ddPCR assay performed were 12 for LTx1, 16 for LTx3, and 18 for LTx6. The results of five different informative assays were used to determine the graft cfDNA content. The percentage of graft cfDNA was always <15% from day 10 onwards if no complications occurred.

Figure 5:
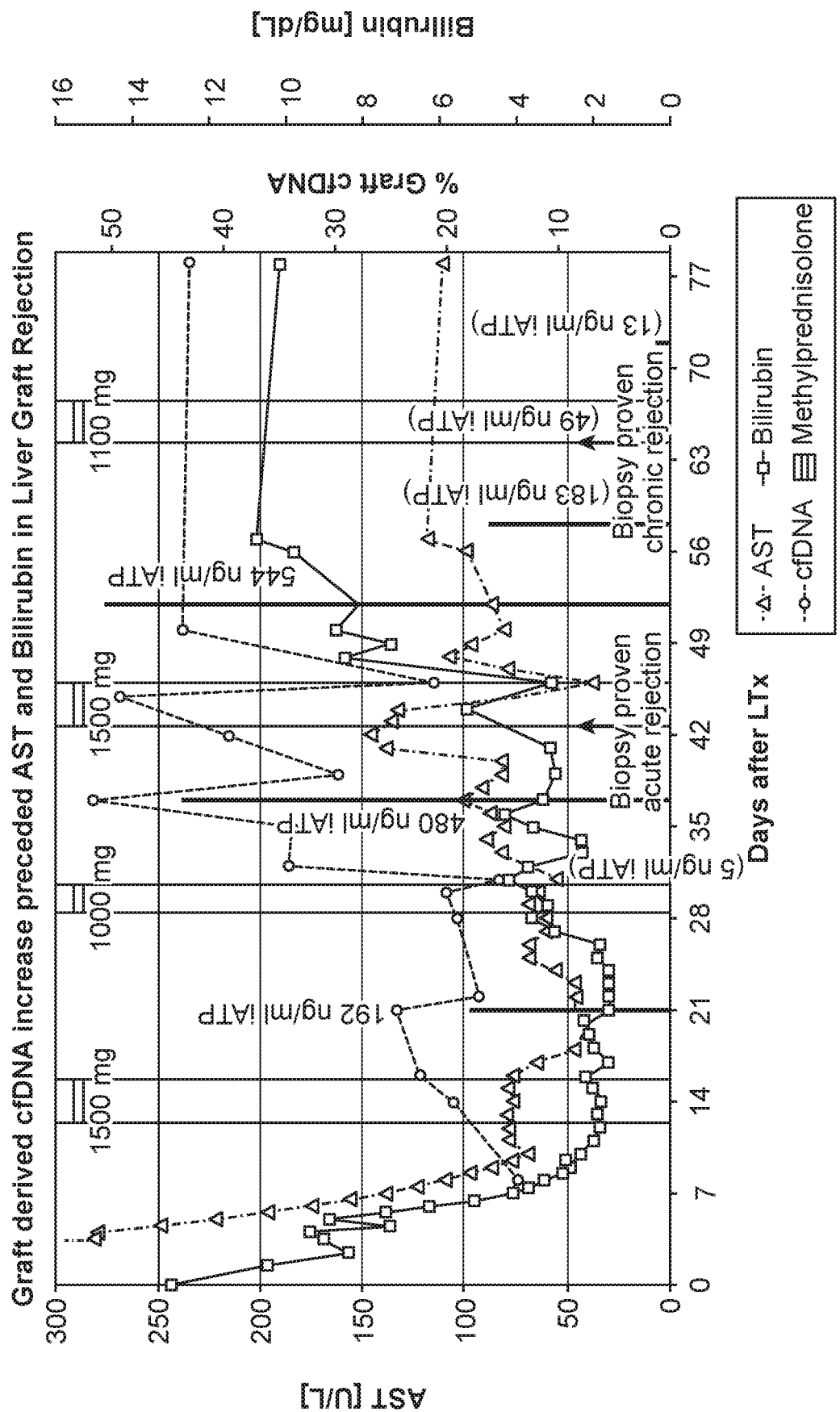
FIG. 5 provides illustrative data from a timecourse measurement of one LTx patient with an acute rejection episode at day 43 after surgery. Graft cfDNA content shows a marked increase on day 32 well before conventional biomarkers AST and bilirubin indicate the rejection.

In contrast, one patient had some presumed early rejection episodes that were proven by biopsy at day 42 after LTx. A total of 16 ddPCR assays were performed for this patient. Five different informative assays were averaged in order to obtain the graft cfDNA content. FIG. 5 displays the time course of the conventionally used sensitive rejection markers bilirubin and AST (aspartate aminotransferase) together with the percentage of graft cfDNA in this patient. After having an initial graft cfDNA value of ~15% on day 7, the values increased and never returned to values seen in the uncomplicated patients during the entire observation period. Moreover, this percentage was markedly increased on day 32, several days before the conventional parameters suggested possible rejection.

This example thus illustrates the identification of SNPs to evaluate transplant status and demonstrated that there was a significant increase of graft cfDNA that preceded AST and bilirubin elevations in a case of LTx rejection. Thus, a cost effective technique was developed that can determine relative amounts of graft DNA in cfDNA of LTx patients in one working day.

This technique makes graft cfDNA a promising biomarker for early detection of rejection, potentially enabling more timely therapeutic intervention.

Example 2. Further Analysis of cfDNA—Quantification of GcfDNA as Copies/mL

Where the ratio of graft to host cfDNA has analytical advantages by eliminating disturbing variables, such as DNA extraction efficiency, variablities in host cfDNA may obfuscate the view on the engrafted organ. The early phase after transplant was used as model to compare the percentage or absolute plasma concentration of GcfDNA is a more valuable graft integrity measure.

Materials and Methods

Blood samples from patients after liver (LTx), heart (HTx) and kidney (KTx) were drawn according to IRB approved protocols. Samples (288) from 23 LTx were included for evaluation of the potency to measure copy numbers of GcfDNA in the initial post-operative phase. For the cfDNA extraction investigations, pools from normal volunteers were used.

EDTA-whole blood was drawn and processed within 4 hours. For LTx patients, cfDNA tubes (9 mL) Streck Inc. were used for a subset of samples. Extraction of cfDNA from 1-2.5 ml of plasma was performed using the High Pure Viral Extraction Large Volume Kit (Roche) according to the manufacturer's instructions, but without the addition of carrier RNA.

For the in-assay assessment of the extraction yield, an artificial DNA (referred to as a "spike" in the example) was added to samples in a known quantity. The spike consisted of a non-human derived 320 bp DNA that was cloned into a pGEM-T vector (Promega) and produced using Phusion polymerase (NEB) with m13 primers. The resulting product was cleaned using AMPure XP (Beckman-Coulter) purification and stored in a 1,400,000-fold concentration of the final spike dilution used for extraction. Prior to each extraction, the spike was diluted and 20 µL were added to the plasma just prior to adding the protease and binding buffer. This resulted in an approximate amount of 5,000 spike copies per mL of plasma.

For the quantification of total cfDNA, two non-SNP-specific assays of single copy genes were used in ddPCR together with the quantification of the internal standard in one assay. 20 µl of the spike-dilution used for the respective extraction was diluted to a final volume of 50 µL using $H_2O$ three times and each independent dilution was measured in ddPCR duplicates. The cfDNA was corrected for the PCR length based efficacy of 98 bp and 90 bp, based on the published size distribution (Beck, et al. *Clin Chem* 55:730-38, 2009). A second primer set of 223 bp and 224 bp that targets the same genetic regions was used to assess the presence of longer DNA fragments in the cfDNA extracts. The ratio between cp/mL determined using the long amplicon assays versus the short amplicon assays was calculated as a measure of necrotic DNA content. The GcfDNA was the calculated by multiplying the GcfDNA [%] with the cfDNA [cp/mL] divided by the extraction efficiency of the internal standard.

GcfDNA [%] was measured as described (Beck et al., *Clin Chem* 59:1732-41, 2013) on a QX100/200 system, which was used for all other described ddPCR assays throughout the study.

Results

Figure 6:
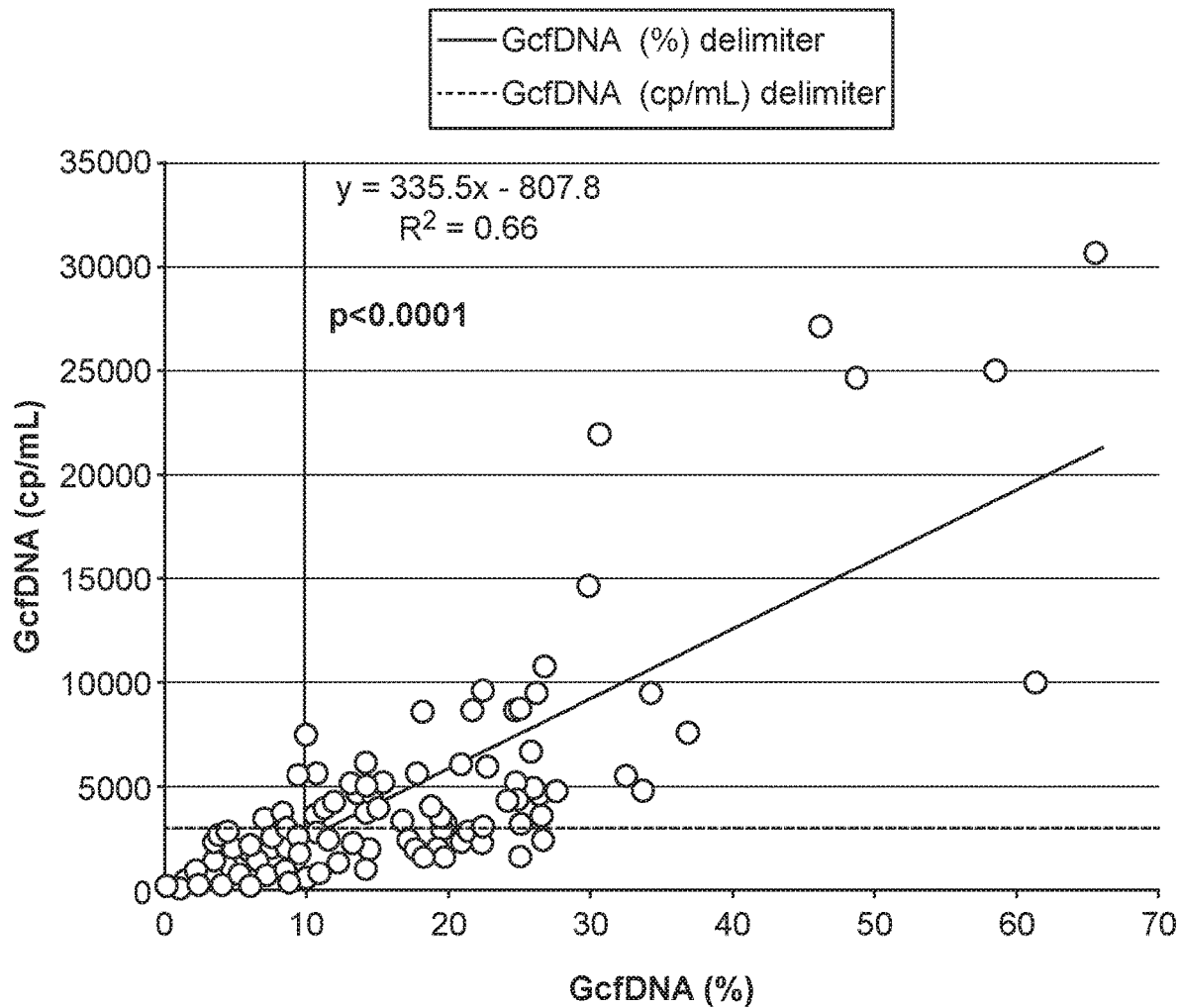
FIG. 6 provides illustrative data comparing graft cfDNA measured as copies/ml to those values expressed as percentage.

When GcfDNA measured as copies/ml were compared with those values expressed as percentage, a correlation of r=0.81 was observed in samples from LTx patients from day 6 post surgery onward. (FIG. 6). The closest value that would be comparable to the 10% delimiter used in the percentages was defined as being 3,000 cp/mL for LTx patients from day 6 post surgery onward.

Example 4—Use of GcfDNA SNP Analysis to Optimize Immunosuppressive Therapy

Immunosuppression minimization requires tools to assess the minimal necessary exposure in individual patients. Drug concentrations and conventional markers are not precise predictors for this purpose. Therefore, in the present study a new practical and cost-effective method for determination of graft-derived cell-free DNA (GcfDNA) was investigated as a sensitive marker of graft injury after liver transplantation (LTx).

Methods: GcfDNA was quantified (n=171) using droplet digital PCR assay in N=12 adult patients predominantly during the early phase (days 8-30) after LTx to determine the amount of graft DNA. Values obtained in patients with various causes of graft dysfunction (i.e. hepatitis C infection [HCV+], cholestasis, low tacrolimus concentrations, and rejection) were compared to a published cut-off (10%) from a historical control group (N=10) of stable adult LTx patients without any clinical or laboratory indications of graft dysfunction or rejection.

The results showed that subtherapeutic tacrolimus levels <8 μg/L, HCV+, and rejection episodes, but not cholestasis, were associated with significantly elevated GcfDNA. Furthermore, significant elevations of GcfDNA were observed 4-6 days before acute rejection was diagnosed.

Figure 7:
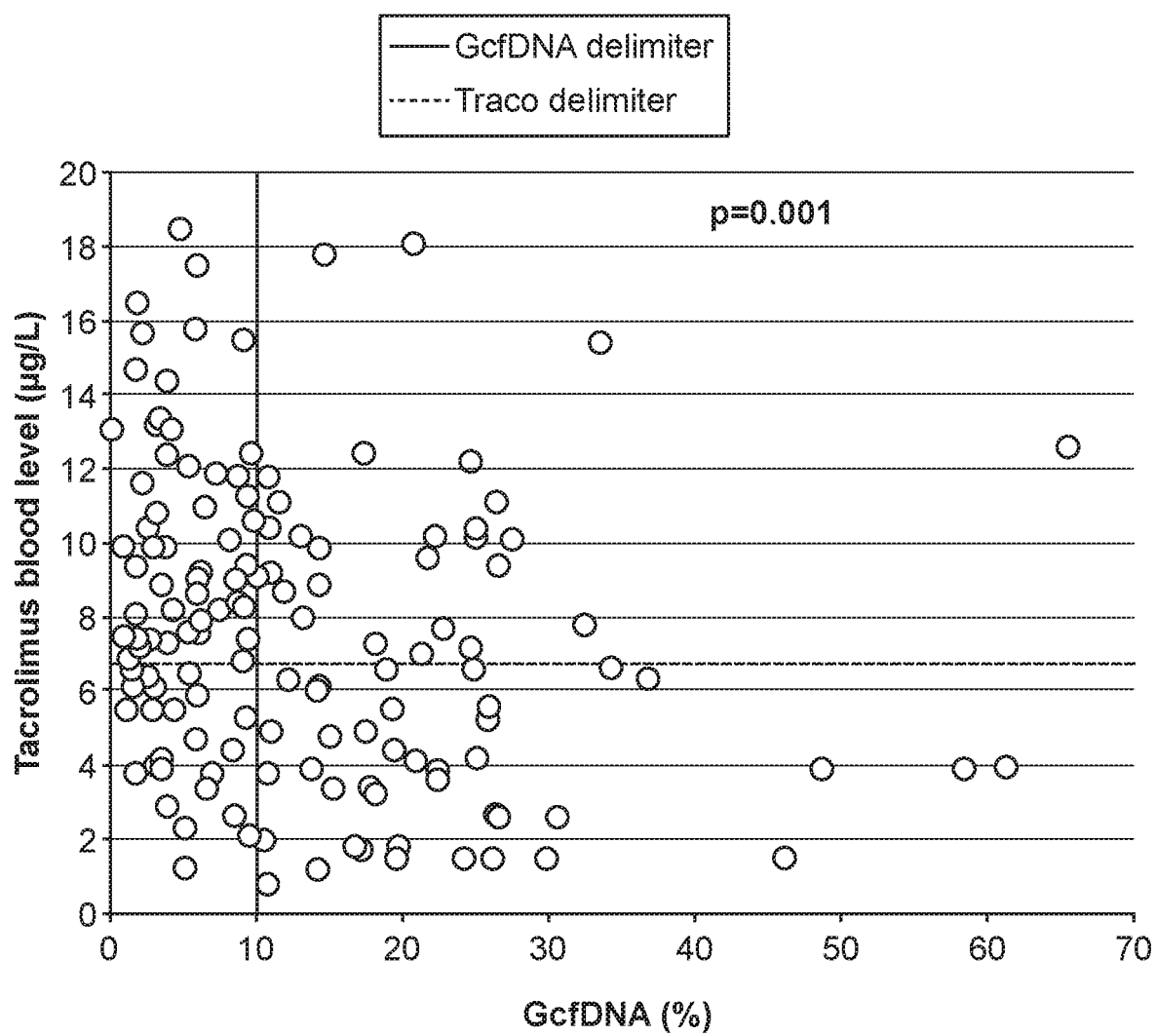
FIGS. 7 and 8 provide illustrative data showing that sub-therapeutic Tacrolimus blood levels are associated with both graft cfDNA (%) (FIG. 7) as well as graft cfDNA copy number (FIG. 8).
Figure 8:
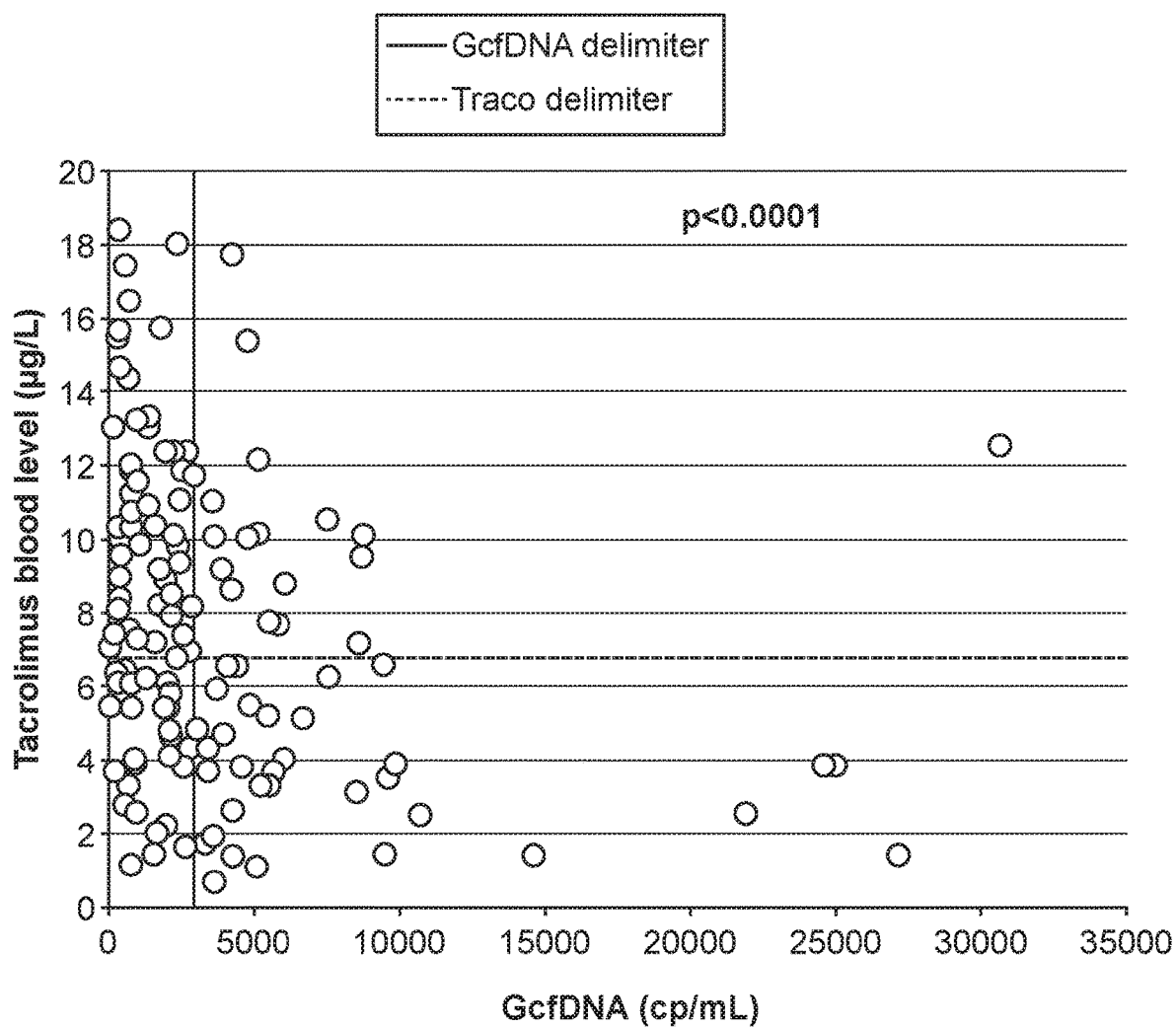
Figure 9:
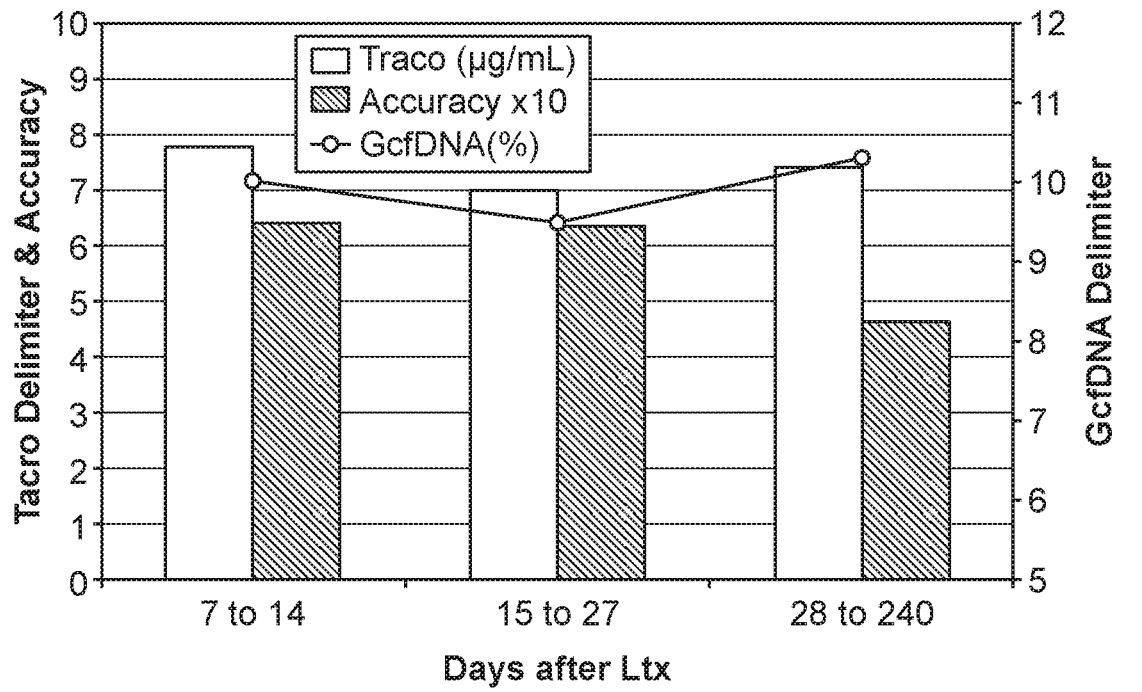
FIG. 9 provides illustrative data showing graft cfDNA copy number at various times after liver transplant.
Figure 9:
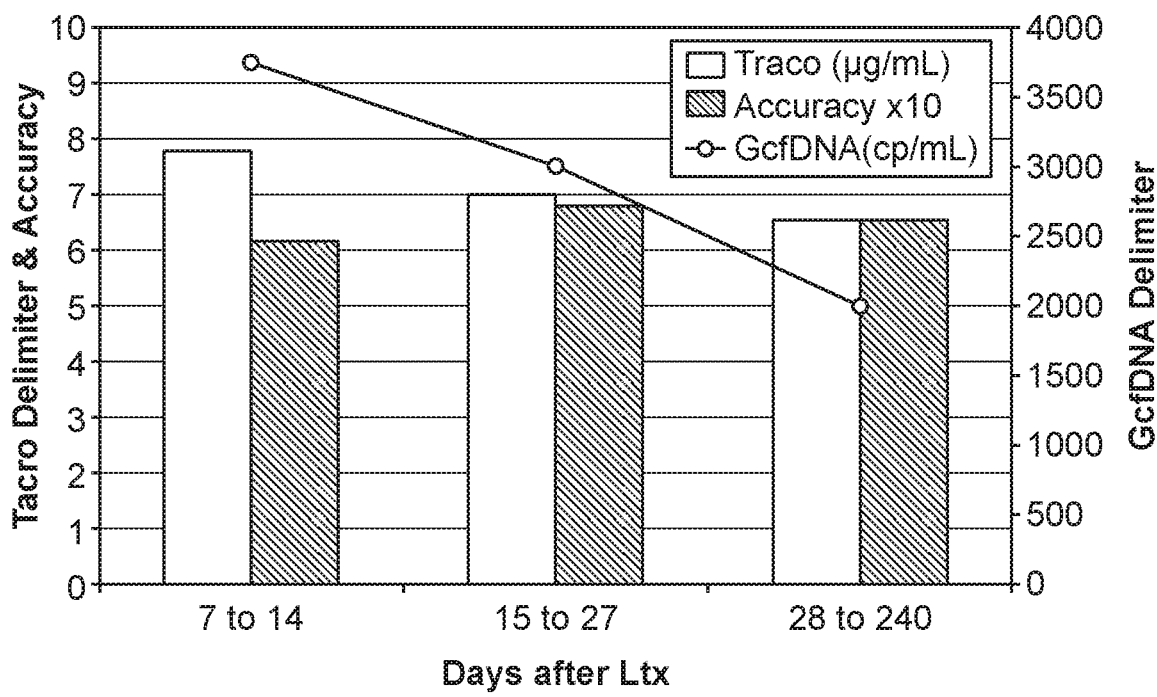

In an attempt to optimize the immunosuppressive therapy, the GcfDNA values in LTx patients were compared with the determined Tacrolimus levels at the same time point (Oellerich et al., *Ther Dug Monit* 36:136-140, 2014). It can be shown that sub-therapeutic Tacrolimus blood levels are associated with both elevated GcfDNA (%) as well as GcfDNA (cp/ml) values. In an extention of the report by Oellerich et al, to evaluate 260 sample, the separation was found to be slightly better with the absolute (cp/mL) determinations (FIGS. 7 and 8), if a Tacrolimus blood level of 6.7 μg/mL was used. Both ways (percentage and copy number) of GcfDNA determinations were useful as an aid in guiding the immunosuppressive drug therapy towards the needed minimal blood level, where no injury is detectable. When stratified over time, the total predictive accuracy as defined by the sum of the samples that are >the delimiter of GcfDNA and <the delimiter of Tacrolimus and <the delimiter of GcfDNA and >the delimiter of Tacrolimus, divided by all samples, a slightly better trend was seen for the cp/mL expression. The limit of GcfDNA (cp/ml) depends on the time after LTx, as the needed Tacro level to control the immune system is (FIG. 9).

These results show that GcfDNA is suitable for the rapid, specific, and early detection of graft injury after LTx and is a useful measure of individual responses to immunosuppressive therapy. Accordingly, the method can be used for the assessment of lowest effective immunosuppressant exposure in minimization strategies.

Example 5. GcfDNA Quantification to Assess Reperfusion Injury

During the initial phase after transplantation, it is assumed that an initial damage is due to cold organ procurement with consecutive warm reperfusion. During cold preservation it is likely that a certain number of hepatocytes will enter a necrotic state and cannot survive the reperfusion phase, which is mostly dominated by apoptotic processes that are initiated during cold storage. An assessment of the severity of this early damage is difficult by conventional liver function tests (LFT), since the hepatocytes are both the production side as well as the affector cells of the damage. Further, the disparity between the number of potential organ recipients and the number of available donor organs has resulted in the increasing use of organs from marginal donors. This example demonstrates the associations found between the clinical course and quantified graft-derived cell-free DNA (GcfDNA) as biomarker of graft integrity in a liver transplant (LTx) patient who received a marginal donor liver and the severity of early damage due to reperfusion.

Figure 10:
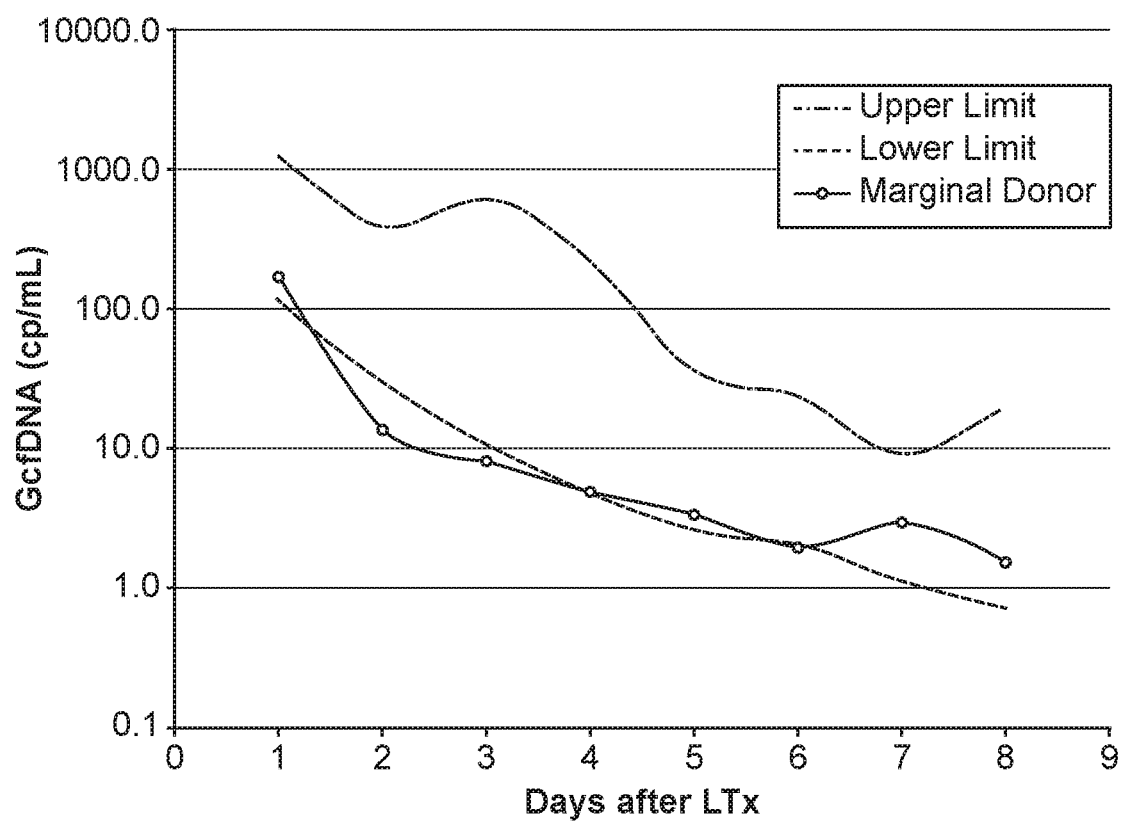
FIG. 10 shows the results obtained from graft cfDNA analysis of the transplant status of a transplant recipient who received a marginal donor organ in comparison to the range seen in fourteen other patients.
Figure 11:
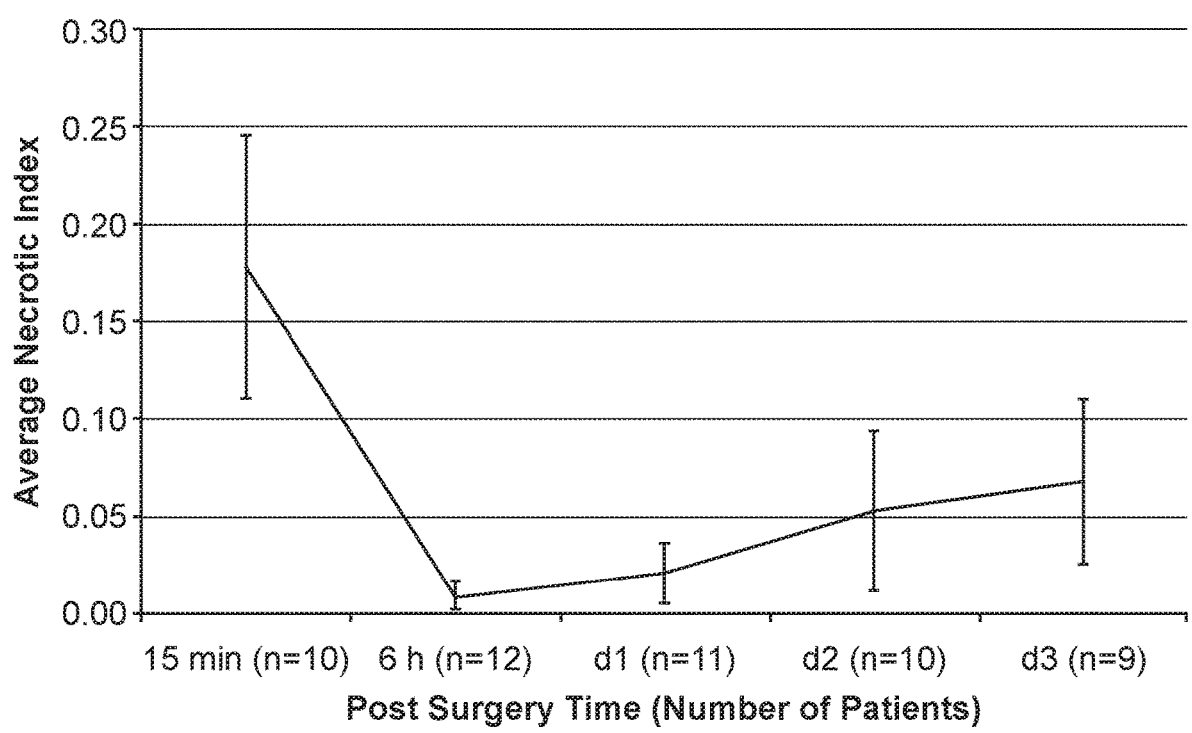
FIG. 11 provides illustrative data showing the time course of necrotic graft cfDNA during the first days after LTx.

The effect of early damage can be quantified by the determination of the GcfDNA (cp/mL), which shows a clear reduction over the first week after LTx. FIG. 10 shows the results obtained from an analysis of a marginal donor in comparison to the range seen in 14 other patients. The LTx of this marginal organ did show a good initial outcome and function, which is predicted by the rapid decrease of GcfDNA at the lower end of the whole group. In addition, the amount of necrosis of the graft can be assessed by estimating the length of the cfDNA, which is short if released by apoptotic cell damage and longer if of necrotic origin. By comparing the amount of cfDNA determined with a digital droplet PCR of short length with those determined with a PCR directed to a longer target, an apoptotic index can be defined. The higher that value is, the more cfDNA is of necrotic origin. FIG. 11 shows the time course during the first days after LTx.

A comparison of the AUC (d1-d5) of GcfDNA percentage and concentration with cold ischemia time, warm ischemia time, age of donor and recipient as well as AST in a multivariate regression showed a better F-value with absolute GcfDNA ($F=5.8;p<0.05$) compared to percentages ($F=0.8;p=0.6$).

The disparity between the number of potential organ recipients and the number of available donor organs has resulted in the increasing use of organs from marginal donors.

Overall in the initial phase after LTx the absolute level of GcfDNA was an effective predictor of ischemia/reperfusion damage, with the capability of assessing the initial graft function and, importantly, the function over time if marginal organs are engrafted.

These results indicate that GcfDNA determinations can be used to monitor early graft recovery and subsequent damage as well as responses to therapeutic interventions. Furthermore, GcfDNA was an immediate and sensitive indicator of compromised graft perfusion. This test can be used as a "liquid biopsy" to assess the integrity of the transplanted organ, especially in recipients of marginal donor livers.

All accession numbers, patents, patent applications, and other published reference materials cited in this specification are hereby incorporated herein by reference in their entirety for their disclosures of the subject matter in whose connection they are cited herein.

What is claimed is:

1. A method of quantifying the amount of donor DNA in a cell-free blood sample of a recipient of a transplanted organ from a donor without genotyping a sample obtained from said donor, the method comprising:
   (a) identifying that one or more SNPs of a panel of SNPs preselected to have a minor allele frequency of 0.4 or greater across human populations are homozygous in the recipient;
   (b) performing a reaction comprising digital PCR to quantify the one or more SNPs identified in (a), in a cfDNA preparation from a blood sample from which cells have been removed obtained from the recipient following transplantation of donor tissue to the recipient, to detect the level of an alternative allele to the allele present in the recipient, wherein detecting the level of the alternative allele comprises counting the DNA molecules that comprise the alternative allele compared to those that comprise the allele present in the recipient;
   wherein the amount of donor DNA in the cell-free cell sample is quantified without genotyping a donor specific sample.

2. The method of claim 1, further comprising a step of amplifying cfDNA from the blood sample to generate a cf library.

3. The method of claim 1, wherein step (a) is performed using DNA isolated from peripheral blood leukocytes obtained from the recipient.

4. The method of claim 1, wherein step (b) comprises performing droplet digital PCR.

5. The method of claim 1, wherein the level of the alternative allele is determined as a percentage of total cfDNA.

6. The method of claim 1, wherein the at least one SNP having an alternative allele quantified in (b) is homozygous in the donor.

7. The method of claim 1, wherein the level of the alternative allele is determined as a concentration.

8. The method of claim 1, further comprising obtaining cfDNA from a further blood sample from which cells have been removed from the recipient following transplantation of donor tissue; and
   quantifying the level of the alternative allele for the at least one SNP of (b) in a cfDNA preparation from the further blood sample.

9. The method of claim 8, wherein the quantifying step comprises determining a concentration of the alternative allele in the cfDNA preparation from the further blood sample.

10. The method of claim 8, wherein the quantifying step comprises determining the percentage of the alternative allele in the cfDNA preparation from the further blood sample.

11. The method of claim 8, wherein the transplanted material is a marginal organ.

12. The method of claim 8, wherein the further blood sample is obtained at least seven days following transplant.

13. The method of claim 8, wherein the further blood sample is obtained a year or longer following transplant.

14. The method of claim 12, further comprising adjusting an administration schedule or dosage of an immunosuppressive drug.

15. The method of claim 8, further comprising detecting donor-specific antibodies in the blood of the recipient.

16. The method of claim 1, wherein the blood sample is obtained at least five days following transplant.

17. The method of claim 1, wherein the transplanted organ is a marginal organ.

18. The method of claim 1, wherein the transplanted organ is a heart, liver, or kidney.

19. The method of claim 1, wherein the blood sample is serum.

20. The method of claim 1, wherein the blood sample is plasma.

21. The method of claim 8, wherein the further blood sample is serum.

22. The method of claim 8, wherein the further blood sample is plasma.

* * * * *